(12) United States Patent
Zhou

(10) Patent No.: US 12,357,691 B2
(45) Date of Patent: Jul. 15, 2025

(54) ANTIBODIES SPECIFICALLY BINDING TO CD147 AND USES THEREOF

(71) Applicant: Alphelix Biotech Co., Ltd., Guangdong (CN)

(72) Inventor: Xiangai Zhou, Guangdong (CN)

(73) Assignee: Alphelix Biotech Co., Ltd., Guangdong (CN)

( * ) Notice: Subject to any disclaimer, the term of this patent is extended or adjusted under 35 U.S.C. 154(b) by 0 days.

(21) Appl. No.: 18/887,598

(22) Filed: Sep. 17, 2024

(65) Prior Publication Data

US 2025/0009878 A1    Jan. 9, 2025

Related U.S. Application Data

(63) Continuation of application No. PCT/CN2023/080437, filed on Mar. 9, 2023.

(30) Foreign Application Priority Data

Mar. 18, 2022 (WO) ............... PCT/CN2022/081835
Mar. 18, 2022 (WO) ............... PCT/CN2022/081836

(51) Int. Cl.
*A61K 39/395* (2006.01)
*A61K 39/00* (2006.01)
*A61P 35/00* (2006.01)
*C07K 16/28* (2006.01)

(52) U.S. Cl.
CPC ........ *A61K 39/39558* (2013.01); *A61P 35/00* (2018.01); *C07K 16/2818* (2013.01); *C07K 16/2878* (2013.01); *A61K 2039/507* (2013.01); *C07K 2317/24* (2013.01)

(58) Field of Classification Search
CPC ........ A61K 39/39558; A61K 2039/507; A61P 35/00; C07K 16/2818; C07K 16/2878; C07K 2317/24
See application file for complete search history.

(56) References Cited

U.S. PATENT DOCUMENTS

2017/0101469 A1    4/2017   Chen et al.
2018/0303952 A1   10/2018   Sagert et al.

FOREIGN PATENT DOCUMENTS

WO    2005/092381 A1    10/2005
WO    2015/160853 A2    10/2015
WO    2019/173771 A1     9/2019

OTHER PUBLICATIONS

Lian et al. Targeting CD147 is a Novel Strategy for Antitumor Therapy. Curr Pharm Des. Nov. 16, 2017;23(29):4410-4421. (Year: 2017).*
Lin et al. Improved affinity of a chicken single-chain antibody to avian infectious bronchitis virus by site-directed mutagenesis of complementarity-determinig region H3. African J Biotech, 2011, 10(79): 18294-18302. (Year: 2011).*
Landras et al. CD147 Is a Promising Target of Tumor Progression and a Prognostic Biomarker. Cancers. 2019; 11(11):1803. (Year: 2019).*
Warram et al. Antibody-based imaging strategies for cancer. Cancer Metastasis Rev 33, 809-822 (2014) (Year: 2014).*
Weidle et al. Cancer-related issues of CD147. Cancer Genomics Proteomics. May-Jun. 2010;7(3):157-69. (Year: 2010).*
Feng et al., "Metuzumab enhanced chemosensitivity and apoptosis in non-small cell lung carcinoma," *Cancer Biology & Therapy* 18(1):51-62, 2017.
Walter et al., "An epitope-specific novel anti-EMMPRIN polyclonal antibody inhibits tumor progression," *Oncoimmunology* 5(2):E1078056, 12 pages, 2016.

* cited by examiner

*Primary Examiner* — Anand U Desai
*Assistant Examiner* — Amber K Faust
(74) *Attorney, Agent, or Firm* — Seed IP Law Group LLP

(57) ABSTRACT

The present disclosure relates to antibodies specifically binding to CD147 or antigen-binding fragment thereof, and a method of treating a disease or condition in a subject in need thereof, comprising administering to the subject an anti-CD147 antibody or antigen-binding fragment, or a polynucleotide encoding the anti-CD147 antibody or antigen-binding fragment, or a pharmaceutical composition comprising the anti-CD147 antibody or antigen-binding fragment or the polynucleotide; use of the anti-CD147 antibody or antigen-binding fragment thereof, or the polynucleotide in the manufacture of a pharmaceutical or kit for treating a disease or condition; as well as of use the combination of the anti-CD147 antibody or antigen-binding fragment thereof, or the polynucleotide, and a MCT inhibitor in the manufacture of a pharmaceutical or a kit for treating a disease or condition.

17 Claims, 14 Drawing Sheets

Specification includes a Sequence Listing.

ID
ANTIBODIES SPECIFICALLY BINDING TO CD147 AND USES THEREOF

CROSS-REFERENCE TO RELATED APPLICATIONS

The present application is a continuation application of International Application No. PCT/CN2023/080437, filed on Mar. 9, 2023, which is based upon and claims priority to International Application Nos. PCT/CN2022/081835 and PCT/CN2022/081836, entitled "ANTIBODIES SPECIFICALLY BINDING TO CD147 AND USES THEREOF" filed on Mar. 18, 2022, which are incorporated by reference in their entireties.

REFERENCE TO AN ELECTRONIC SEQUENCE LISTING

The contents of the electronic sequence listing (110341_401C1_Seq_v2.xml; Size: 32,416 bytes; and Date of Creation: Dec. 26, 2024) is herein incorporated by reference in its entirety.

FIELD OF THE INVENTION

The present disclosure relates to the field of biomedicine. In particular, the present disclosure relates to anti-CD147 antibodies and use thereof.

BACKGROUND OF THE INVENTION

Monocarboxylates play important roles in wide range of activities including energy metabolism and cell signaling. The transmembrane movements of the monocarboxylates in mammals are catalyzed by two types of solute carriers (SLCs), the proton-coupled monocarboxylate transporters (MCTs) that belong to solute carrier 16 (SLC16) family, and the sodium-coupled monocarboxylate transporters (SMCTs) that belong to solute carrier 5 (SLC5) family. Among 14 identified MCTs, MCTs 1-4 have been extensively studied as they selectively transport products of the glycolysis cycle including lactate, pyruvate, and ketone bodies. The net transport direction of substrates is determined by cross-membrane concentration gradients of protons and monocarboxylates.

Lactic acid or lactate produced by aerobic glycolysis plays an important role in tumor growth and microenviromnent maintenance. MCTs 1-4, are the major lactate shuttles in human body, therefore physiologically critical to the lactate homeostasis at the tissue and the organismal levels. At the tissue level, lactate concentration in the circulation is tightly controlled to avoid the lactic acidosis, a serious medical condition. Moreover, the lactate exchange between the circulation and the tissues regulates not only the circulating lactate concentration, but also lactate localization in the tissues and thus allows for independent operation of glycolysis and the TCA cycles in the tissues. At the organismal level, lactate shuttling between glycolytic cells and oxidative cells sustains a tight balance between production by glycolysis and consumption by the TCA cycle.

MCTs 1 and 4 are overexpressed in a number of cancers and promote tumor growth and aggressiveness through multiple aspects. Tumor cells usually establish metabolic symbiosis of lactate, whereby the oxidative cancer cells preferentially use lactate as an oxidative fuel and thus spare glucose for the glycolytic cancer cells or cancer-associated fibroblasts (CAFs) that in turn convert glucose to lactate for the oxidative cancer cells. MCTs 1 and 4 are the critical lactate shuttles to sustain this symbiosis. Moreover, MCTs 1 and 4 import lactate into vascular endothelial cells to promote tumor angiogenesis through NF-κB/IL-8 signaling pathway, and export lactate to extracellular niche of tumor to suppress anti-tumor immune responses. Inhibiting the transport activities of MCTs 1 and 4 in cancer cells to prevent the release of lactate into tumor microenvironment (TME) augments activities of effector T cells and improves checkpoint therapies.

Due to the vital roles of MCTs 1 and 4 in lactate homeostasis, inhibition of these MCTs is a promising therapeutic target for cancer treatment. Previous studies have shown that the anchorage and stability of MCTs 1 and 4 on plasma membrane require their physical interaction with basigin (BSG). BSG, also known as cluster of differentiation 147 (CD147), is a single pass transmembrane protein of the immunoglobulin (Ig) superfamily that plays pivot roles in reproduction, neural function, pathogen infection, and T cell activation and proliferation. The BSG-2, which encodes two extracellular Ig domains is the most predominant splice variant of BSG that is tightly associated with MCT1 or MCT4. BSG-2 is highly expressed in many cancer cells, stimulating the production of vascular endothelial growth factor (VEGF) and the expression of the matrix metalloproteinases to promote tumor angiogenesis and proliferation. BSG-2 has become a target of treating hepatocellular carcinoma (HCC) in clinical trial.

There is umnet need to provide a therapeutic agent to inhibit MCT1, MCT4, and/or CD147, in order to treat a disease or condition.

SUMMARY OF THE INVENTION

The present disclosure relates to an anti-CD147 antibody or antigen-binding fragment thereof, and use of the anti-CD147 antibody or antigen-binding fragment thereof for treatment of a disease or condition.

Certain aspects of the present disclosure are directed to an anti-CD147 antibody or antigen-binding fragment thereof comprising a heavy chain CDR1 having the amino acid sequence set forth in SEQ ID NO:1, a heavy chain CDR2 having the amino acid sequence set forth in SEQ ID NO:2, a heavy chain CDR3 having the amino acid sequence set forth in SEQ ID NO:3, a light chain CDR1 having the amino acid sequence set forth in SEQ ID NO:4, a light chain CDR2 having the amino acid sequence set forth in SEQ ID NO:5 and a light chain CDR3 having the amino acid sequence set forth in SEQ ID NO:6.

Certain aspects of the present disclosure are directed to a polynucleotide encoding the antibody or antigen-binding fragment thereof according to the present disclosure.

Certain aspects of the present disclosure are directed to a pharmaceutical composition comprising the anti-CD147 antibody or antigen-binding fragment thereof according to the present disclosure or the polynucleotide according to the present disclosure, and a pharmaceutically acceptable carrier.

Certain aspects of the present disclosure are directed to a kit, comprising the anti-CD147 antibody or antigen-binding fragment according to the present disclosure or the polynucleotide according to the present disclosure or the pharmaceutical composition according to the present disclosure. In some embodiments, the kit provided herein includes a MCT inhibitor and/or an immune checkpoint blockade therapeutic agent.

Certain aspects of the present disclosure are directed to a method of preventing, diagnosing, or treating a disease or condition in a subject in need thereof, comprising administering to the subject an anti-CD147 antibody or antigen-binding fragment, or a polynucleotide encoding the anti-CD147 antibody or antigen-binding fragment, or a pharmaceutical composition comprising the anti-CD147 antibody or antigen-binding fragment or the polynucleotide.

Certain aspects of the present disclosure are directed to use of an anti-CD147 antibody or antigen-binding fragment thereof, or a polynucleotide encoding the anti-CD147 antibody or antigen-binding fragment, or the pharmaceutical composition provided herein in the manufacture of a pharmaceutical/therapeutic agent or kit for diagnosing, preventing, or treating a disease or condition. Certain aspects of the present disclosure are directed to use of the combination of an anti-CD147 antibody or antigen-binding fragment thereof, or a polynucleotide encoding the anti-CD147 antibody or antigen-binding fragment, or the pharmaceutical composition provided herein, and a MCT inhibitor in the manufacture of a pharmaceutical or a kit for treating a disease or condition.

Certain aspects of the present disclosure are directed to use of the combination of an anti-CD147 antibody or antigen-binding fragment thereof, or a polynucleotide encoding the anti-CD147 antibody or antigen-binding fragment, or the pharmaceutical composition provided herein, and an immune checkpoint blockade therapeutic agent in the manufacture of a pharmaceutical or a kit for treating a disease or condition.

DETAILED DESCRIPTION OF CERTAIN EMBODIMENTS

Figures 1, 2:
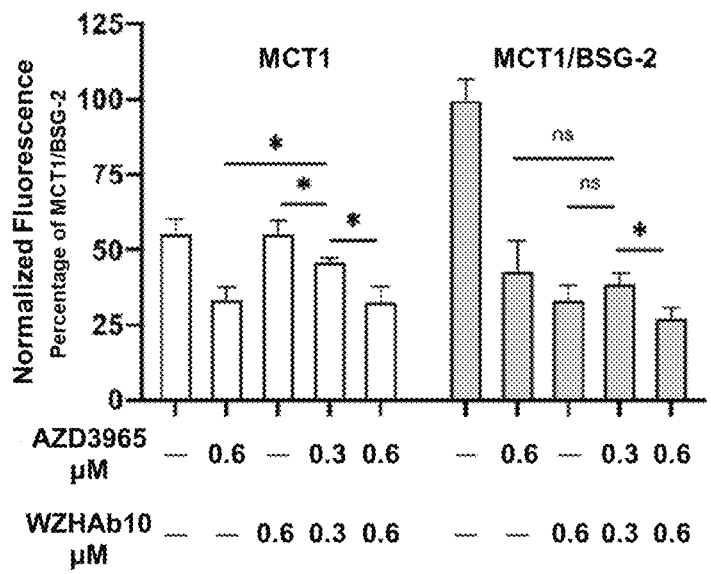
FIG. 1 shows amino acid sequence alignment of human BSG-2 with other vertebrate orthologs (bovine, chick, hamster, rat, rabbit, mouse; SEQ ID NOs:19-25).
FIG. 2 shows H+ influx mediated by MCT1 and MCT1/BSG-2 in presence of WZHAb10, or AZD3965, or both, demonstrating inhibiting efficacy of WZHAb10 and AZD3965 on MCT1.

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth.

Unless defined otherwise, all technical and scientific terms used herein have the same meaning as commonly understood by one of ordinary skill in the art to which this disclosure is related.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions.

The term "amino acid" is intended to embrace all molecules, whether natural or synthetic, which include both an amino functionality and an acid functionality and capable of being included in a polymer of naturally occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "activity" includes activities such as the binding specificity/affinity of an antibody.

The terms "the proton-coupled monocarboxylate transporters" and "MCTs" are used belong to solute carrier 5 (SLC5) family. Among 14 identified MCTs, MCTs 1-4 have been extensively studied as they selectively transport products of the glycolysis cycle including lactate, pyruvate, and ketone bodies. MCTs 1-4, are the major lactate shuttles in human body, therefore physiologically critical to the lactate homeostasis at the tissue and the organismal levels.

MCTs 1 and 4 are overexpressed in several cancers and promote tumor growth and aggressiveness through multiple aspects. Tumor cells usually establish metabolic symbiosis of lactate, whereby the oxidative cancer cells preferentially use lactate as an oxidative fuel and thus spare glucose for the glycolytic cancer cells or cancer-associated fibroblasts (CAFs) that in turn convert glucose to lactate for the oxidative cancer cells. MCTs 1 and 4 are the critical lactate shuttles to sustain this symbiosis. The vital roles of MCTs 1 and 4 in lactate homeostasis, inhibition of these MCTs is a promising therapeutic target for cancer treatment.

The anchorage and stability of MCTs 1 and 4 on plasma membrane require their physical interaction with basigin (BSG).

The terms "BSG", "Basigin" and "CD147" is used describe a single pass transmembrane protein of the immunoglobulin (Ig) superfamily that plays pivot roles in reproduction, neural function, pathogen infection, and T cell activation and proliferation. The BSG-2, which encodes two extracellular Ig domains is the most predominant splice variant of BSG that is tightly associated with MCT1 or MCT4. BSG-2 is highly expressed in many cancer cells, stimulating the production of vascular endothelial growth factor (VEGF) and the expression of the matrix metalloproteinases to promote tumor angiogenesis and proliferation. BSG-2 has become a target of treating hepatocellular carcinoma (HCC) in clinical trial. The CD147 molecule may be closely associated with tumour progression and recurrence.

The terms "cancer" and "tumor" can be used interchangeably. For example, both terms encompass solid and liquid tumors. As used herein, the term "cancer" or "tumor" includes premalignant, as well as malignant cancers and tumors.

The terms "DLBCL" and "Diffuse large B-cell lymphoma" are used describe an aggressive (fast-growing) non-Hodgkin lymphoma (NHL) that affects B-lymphocytes. Lymphocytes are one type of white blood cell. B-cells are lymphocytes that make antibodies to fight infections and are an important part of the lymphatic system.

Diffuse large B-cell lymphoma (DLBCL) is the most common type of non-Hodgkin lymphoma (NHL) in the United States and worldwide, accounting for about 22 percent of newly diagnosed cases of B-cell NHL in the United States. More than 18,000 people are diagnosed with DLBCL each year.

The term "NSCLC" refers to any type of epithelial lung cancer other than small cell lung cancer (SCLC). The most common types of NSCLC are squamous cell carcinoma, large cell carcinoma, and adenocarcinoma, but there are several other types that occur less frequently, and all types can occur in unusual histologic variants.

The term "Melanoma" refers to a form of skin cancer distinguished by abnormal expression of melanocyte cells, which are responsible for producing pigmentation in the skin. Melanoma is the deadliest form of any skin cancer, with a five-year survival rate of under 20% for cases diagnosed in late stages. Roughly half of all melanoma diagnosis are considered invasive, and incident level has been increasing significantly over the course of the last few decades. There are many therapeutic agents that are being developed to reduce the incident level and improve standard of care, but there remains to be highly effective treatments for advanced stage melanoma.

The term "transfection" refers to a process by which agents are introduced into a cell. The list of agents that can be transfected is large and includes, but is not limited to, siRNA, sense and/or anti-sense sequences, DNA encoding one or more genes and organized into an expression plasmid, proteins, protein fragments, and more. There are multiple methods for transfecting agents into a cell including, but not limited to, electroporation, calcium phosphate-based transfections, DEAE-dextran-based transfections, lipid-based transfections, molecular conjugate-based transfections (e.g., polylysine-DNA conjugates), microinjection and others.

The term "combination therapy", as used herein, refers to the administration of two or more therapeutic substances, e.g., an anti-CD147 antibody or an antigen-binding fragment and an additional therapeutic agent. The additional therapeutic agent may be administered concomitant with, prior to, or following the administration of the anti-CD147 antibody or an antigen-binding fragment. In one embodiment, the anti-CD147 antibody or an antigen-binding fragment of the invention are administered in combination with one or more inhibitors for the treatment of a tumor.

As used herein, the term "subject" refers to human or non-human animal subjects. Exemplary subjects include humans and mammalians. Exemplary subjects include humans, monkeys, dogs, cats, mice, rats, bovines, chicks, hamsters, horses, camels, goats, rabbits, pigs, and sheep. In certain embodiments, the subject is human, bovine, chick, hamster, rat, rabbit, and mouse. In certain embodiments, the subject is a human. In some embodiments the subject has a disease or condition that can be treated with an antibody provided herein.

Certain aspects of the present disclosure are directed to an anti-CD147 antibody or antigen-binding fragment thereof comprising a heavy chain CDR1 having the amino acid sequence set forth in SEQ ID NO:1, a heavy chain CDR2 having the amino acid sequence set forth in SEQ ID NO:2, a heavy chain CDR3 having the amino acid sequence set forth in SEQ ID NO:3, a light chain CDR1 having the amino acid sequence set forth in SEQ ID NO:4, a light chain CDR2 having the amino acid sequence $X_1X_2VSX_3X_4IX_5$ (SEQ ID NO:5) and a light chain CDR3 having the amino acid sequence set forth in SEQ ID NO:6. In some embodiments, $X_1$, $X_2$, $X_3$, $X_4$, and $X_5$ independently are any amino acid.

In some embodiments, the anti-CD147 antibody or an antigen-binding fragment thereof comprises a heavy chain CDR1 having the amino acid sequence set forth in SEQ ID NO:7, a heavy chain CDR2 having the amino acid sequence set forth in SEQ ID NO:8, a heavy chain CDR3 having the amino acid sequence set forth in SEQ ID NO:9, a light chain CDR1 having the amino acid sequence set forth in SEQ ID NO: 10, a light chain CDR2 having the amino acid sequence set forth in SEQ ID NO:1 and a light chain CDR3 having the amino acid sequence set forth in SEQ ID NO:12.

In some embodiments, the anti-CD147 antibody or an antigen-binding fragment thereof comprises a heavy chain variable region having the amino acid sequence set forth in SEQ ID NO: 13; and a light chain variable region having the amino acid sequence set forth in SEQ ID NO: 14.

In some embodiments, the anti-CD147 antibody or an antigen-binding fragment thereof comprises a heavy chain constant region having the amino acid sequence set forth in SEQ ID NO: 15; and a light chain constant region having the amino acid sequence set forth in SEQ ID NO: 16.

In some embodiments, the anti-CD147 antibody or an antigen-binding fragment thereof comprises a heavy chain having the amino acid sequence set forth in SEQ ID NO: 17; and a light chain having the amino acid sequence set forth in SEQ ID NO: 18.

Certain aspects of the present disclosure are directed to a polynucleotide encoding the antibody or antigen-binding fragment thereof according to the present disclosure.

Certain aspects of the present disclosure are directed to a pharmaceutical composition comprising the anti-CD147 antibody or antigen-binding fragment thereof describe above, or the polynucleotide describe above, and a pharmaceutically acceptable carrier.

Generally, these substances can be formulated in a non-toxic, inert and pharmaceutically acceptable aqueous carrier medium, wherein the pH is usually about 5-8, preferably about 6-8, although the pH can be changed according to properties of the formulated substances and disease conditions to be treated. The formulated pharmaceutical composition can be administered by conventional routes, including (but not limited to) intratumoral administration, intraperitoneal administration, intravenous administration, or topical administration.

The pharmaceutical composition of the present disclosure contains a safe and effective amount (such as 0.001-99 wt %, preferably 0.01-95 wt %, more preferably 0.1-90 wt %) of the single domain antibody or the fusion protein provided and a pharmaceutically acceptable carrier or excipient. Such carrier includes (but is not limited to) saline, buffer, glucose, water, glycerol, ethanol and combinations thereof. A pharmaceutical preparation should be matched with the administration mode. The pharmaceutical composition of the present application can be prepared into an injection form, for example, the pharmaceutical composition is prepared by conventional methods with physiological saline or an aqueous solution containing glucose and other adjuvants. The pharmaceutical composition such as an injection and a solution should be manufactured under sterile conditions. The dosage of active ingredients is a therapeutically effective amount, such as about 10 μg/kg body weight to about 100 mg/kg body weight per day.

In some embodiments, the pharmaceutical composition comprises an additional therapeutic agent.

In some embodiments, the additional therapeutic agent comprises a MCT inhibitor.

In some embodiments, the MCT inhibitor is MCT1 inhibitor and/or MCT4 inhibitor.

In some embodiments, the pharmaceutical composition includes an immune checkpoint blockade therapeutic agent.

The term "immune checkpoint" refers to a component of the immune system which provides inhibitory signals to its components in order to regulate immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAGS, BTLA, B7H3, B7H4, TIM3, and KIR are recognized in the art to constitute immune checkpoint pathways similar to the CTLA-4 and PD-1 dependent pathways (see e.g., Pardoll, 2012. Nature Rev Cancer 12:252-264; Mellman et al., 2011. Nature 480:480-489).

An immune checkpoint blockade therapeutic agent refers to any compound inhibiting the function of an immune checkpoint protein. Inhibition includes reduction of function and full blockade. In particular, the immune checkpoint protein is a human immune checkpoint protein.

In some embodiments, the pharmaceutical composition includes anti-PD1 antibody, anti-PDL1 antibody, anti-CTLA4 antibody, anti-PDL2 antibody, anti-LAG3 antibody, anti-BTLA antibody, anti-B7H3 antibody, anti-B7H4 antibody, anti-TIM3 antibody and/or anti-KIR antibody. In some embodiments, the pharmaceutical composition includes anti-PD1 antibody or anti-PDL1 antibody.

Certain aspects of the present disclosure are directed to a kit, comprising the anti-CD147 antibody or antigen-binding fragment according to the present disclosure or the polynucleotide according to the present disclosure or the pharmaceutical composition according to the present disclosure.

In some embodiments, the kit includes a MCT inhibitor, such as a MCT1 inhibitor, or a MCT4 inhibitor.

In some embodiments, the kit includes an immune checkpoint blockade therapeutic agent, which including, but not limited to, anti-PD1 antibody or anti-PDL1 antibody.

Certain aspects of the present disclosure are directed to a method of preventing, diagnosing, or treating a disease or condition in a subject in need thereof, comprising administering to the subject the anti-CD147 antibody or antigen-binding fragment according to the present disclosure or the polynucleotide according to the present disclosure or the pharmaceutical composition according to the present disclosure.

In some embodiments, the method includes administering a therapeutically effective amount to the subject of anti-CD147 antibody or antigen-binding fragment, the polynucleotide, or the pharmaceutical composition described above.

The therapeutically effective amount causes a reduction in the severity of disease symptoms and increased frequency and duration of asymptomatic period of a disease, disorder or condition, or prevents injury or disability due to illness or suffering. For example, for the treatment of tumors (including, for example, melanoma, lymphoma, bladder cancer, non-small cell lung cancer, head and neck cancer, and colon cancer), relative to untreated subjects, the "therapeutically effective amount" preferably inhibits the cell growth or tumor growth by at least about 10%, preferably at least about 20%, more preferably at least about 30%, more preferably at least about 40%, more preferably at least about 50%, more preferably at least about 60%, more preferably at least about 70%, more preferably at least about 80%.

In some embodiments, the disease or condition comprises diseases with expression of CD147, MCT1, MCT3, and/or MCT4. In some embodiments, the disease or condition comprises diseases with high expression of CD147, MCT1, MCT3, and/or MCT4.

In some embodiments, the disease or condition includes diseases with expression of immune checkpoint, optionally, PD1 and/or PDL1.

In some embodiments, the disease or condition comprises tumor and infectious disease.

In some embodiments, the tumor comprises prostate cancer, pancreatic cancer, lung cancer, breast cancer, ovarian cancer, stomach cancer, lymphoma, oesophagus cancer, bowel cancer, bone cancer, wherein the infectious disease comprises inflammatory bowel disease, neovirus pneumonia, enteritis caused by *E. coli* and *Salmonella*, measles, listeriosis and *falciparum* malaria.

In some embodiments, the method comprises administering to the subject a MCT inhibitor before, after or at the same time as administration of the anti-CD147 antibody or antigen-binding fragment, or the polynucleotide, or the pharmaceutical composition provided herein.

In some embodiments, the method includes administering to the subject an immune checkpoint blockade therapeutic agent before, after or at the same time as administration of the anti-CD147 antibody or antigen-binding fragment, or the polynucleotide, or the pharmaceutical composition provided herein.

Certain aspects of the present disclosure are directed to use of the anti-CD147 antibody or antigen-binding fragment provided by the present disclosure, or the polynucleotide described above in the manufacture of a pharmaceutical/therapeutic agent or kit for diagnosing, preventing, or treating a disease or condition.

Provided herein is a use of the combination of an anti-CD147 antibody or antigen-binding fragment thereof described above, or a polynucleotide described above, or a pharmaceutical composition described above, and a MCT inhibitor in the manufacture of a pharmaceutical/therapeutic agent or a kit for diagnosing, preventing, or treating a disease or condition.

Provided herein is a use of the combination of an anti-CD147 antibody or antigen-binding fragment thereof described above, or a polynucleotide described above, or a pharmaceutical composition described above, and and an immune checkpoint blockade therapeutic agent in the manufacture of a therapeutic agent or a kit for diagnosing, preventing, or treating a disease or condition.

In some embodiments, the disease or condition comprises diseases with expression of CD147, MCT1, MCT3, and/or MCT4.

In some embodiments, the disease or condition includes diseases with expression of immune checkpoint, such as PD1.

In some embodiments, the disease or condition comprises tumor and infectious disease.

In some embodiments, the tumor comprises, wherein the tumor comprises prostate cancer, pancreatic cancer, lung cancer, breast cancer, ovarian cancer, stomach cancer, lymphoma, oesophagus cancer, bowel cancer, bone cancer, wherein the infectious disease comprises inflammatory bowel disease, neovirus pneumonia, enteritis caused by *E. coli* and *Salmonella*, measles, listeriosis and falciparum malaria.

In some embodiments, the subject includes humans or non-human animals, such as bovine, chick, hamster, rat, rabbit, mouse.

The present disclosure will further be illustrated in the following non-limiting working examples, it being understood that these examples are intended to be illustrative only and that the disclosure is not intended to be limited to the materials, conditions, process parameters and the like recited herein. All proportions are by weight unless otherwise indicated.

EXAMPLES

Example 1: Amino Acid Sequence of BSG Ig2 Domain

Amino acid sequence of BSG Ig2 domain is shown in FIG. 1. Most residues of BSG-2 at interface are highly or moderately conserved across vertebrate orthologs (FIG. 1), suggesting anti-CD147 antibody may bind these orthologues. Therefore, the antibody can be used in humans and other animals.

Selected functionally important amino acid residues interacting with WZHAb10 are annotated for BSG-2. Residues highlighted in grey are engaged in extensive polar and non-polar interactions between BSG-2 and WZHAb10. Residues marked by circle, triangle, and rhombus each contacts multiple residues of WZHAb10 in polar interactions, respectively, and could impair the binding of BSG-2 and WZHAb10 if mutated into alanine residues. WZHAb10 comprises a heavy chain having the amino acid sequence set forth in SEQ ID NO: 17; and a light chain having the amino acid sequence set forth in SEQ ID NO: 18.

Example 2: Preparation of an anti-CD147 antibody

Hybridoma technology was used to develop monoclonal antibodies that can bind BSG-2. MCT1/BSG-2 was chose as the antigen.

(1) Expression and Purification of WT MCTs, WT MCTs in Complexes with WT BSG-2, or MCT1/BSG-2 Mutational Variants The coding sequences for mouse wild type MCT1 (MCT1), MCT4 (MCT4) and BSG-2 (BSG-2) and their mutational or truncational variants were each cloned into pEG BacMam vector that was a gift from Eric Gouaux lab. Unless stated otherwise, 8xHis-Flag tags were located at the C termini of proteins and connected by a Rhinovirus 3C protease-cleavable linker. WT MCTs, WT MCTs in complexes with WT BSG-2, MCT1/BSG-2 variants with point mutations in either protein or both, in this study, was expressed in HEK293S GnTI-(N-acetylglucosaminyl-transferase I-negative) cells (American Type Culture Collection, catalog no. CRL-3022). Cells were collected by centrifugation (5,000×g, 10 min, 4° C.) and disrupted by KIMBLE Dounce tissue grinder (Merck Millipore) in buffer (50 mM HEPES pH7.5, 150 mM NaCl) supplemented with 5.2 µg/mL aprotinin, 2 µg mL$^{-1}$ leupeptin, and 1.4 µg/mL pepstatin A (all from Merck Millipore). Cell debris was removed by centrifugation (10,000×g, 25 min, 4° C.). The membrane fraction was collected by ultracentrifugation (100,000×g, 1 hr, 4° C.), and solubilized for 2.5 h at 4° C. in buffer (50 mM HEPES pH7.5, 150 mM NaCl, 1% (w/v) n-dodecyl-D-maltoside (DDM, Anatrace), 0.1% (w/v) cholesteryl hemisuccinate (CHS, Anatrace)). Insoluble materials were removed by ultracentrifugation (100,000×g, 1 hr, 4° C.). The detergent-soluble fraction was incubated with Ni-NTA resin (Qiagen), and incubated for 2 hr at 4° C. The beads were eluted with elution buffer (20 mM HEPES pH7.5, 150 mM NaCl, 0.03% DDM, 0.003% CHS and 250 mM imidazole), and further incubated for 2 hr with anti-DYKDDDDK G1 Affinity Resin (GenScript) to improve protein purity. The protein sample was then eluted by DYKDDDDK (SEQ ID NO. 26) peptide (Genscript), and purified by size-exclusion chromatography (SEC) on a Superdex 200 Increase 10/300 GL column (GE Healthcare), equilibrated with SEC buffer (20 mM HEPES pH7.5, 150 mM NaCl, 0.03% DDM, 0.003% CHS). The peak fractions of the protein sample were collected and concentrated to 2.0-5.0 mg/mL, using a 100 kDa MWCO Amicon centrifugal filter (Merck Millipore). Each protein or protein complex was flash frozen and stored in liquid nitrogen for further usage.

(2) Expression and Purification of Saposin A

Saposin A in a pNIC28-Bsa4 vector was expressed with an N-terminal 6xHis-tag and thrombin cleavage site in the *E. coli* strain Rosetta-gami BDE3. The cell culture was first grown in terrific broth (TB) media at 37° C. until an OD600 of 1.0, and then induced with 0.4 mM IPTG for protein expression at 18° C. overnight. After harvesting the cells, the pellet was resuspended in buffer (50 mM HEPES pH7.5, 300 mM NaCl, 1% (w/v) Triton X-100 (Merck Millipore)) and then lysed via homogenizer (ATS Engineering Limited, China). The cell suspension was heated to 85° C. for 10 min to precipitate all thermolabile components. Insoluble materials were removed by centrifugation (16 000×g, 20 min, 4° C.). Saposin A containing supernatant was incubated with Ni-NTA resin for 3 hr at 4° C. The beads were washed, and the protein was eluted with buffers with an increasing imidazole concentration (20 mm HEPES pH7.5, 300 mm NaCl, 50 mM sodium cholate, 30/400 mm imidazole). Thrombin (Merck Millipore) was added to the eluted protein and dialyzed overnight at 4° C. against dialysis buffer (20 mm HEPES pH7.5, 300 mm NaCl, 5% glycerol). The cleaved protein was concentrated and purified by SEC on a Superdex 200 Increase 10/300 GL colum (GE Healthcare) equilibrated with SEC buffer (20 mM HEPES pH7.5, 150 mM NaCl). The pure Saposin A was concentrated to 1.0-2.0 mg/mL and stored at −80° C. for further usage.

(3) Reconstitution of WT MCT1/BSG-2 into Salipro Nanoparticles and Preparation of WT MCT1/BSG-2 in Complex with WZHAb10Fab WT MCT1/BSG-2 was reconstituted into Salipro nanoparticle following an established protocol. Briefly, 1-Palmitoyl-2-oleoyl-sn-glycero-3-PC (POPC): 1-palmitoyl-2-oleoyl-sn-glycero-3-phosphoethanolamine (POPE): L-α-phosphatidylglycerol (POPG) lipid mix (3:1:1, all from Avanti) was first resuspended from a dry lipid film in 15 mM cholate to obtain a 10 mM lipid stock solution. Then MCT1/BSG-2:Saposin A:POPC/POPE/POPG lipid mix in a molar ration of 1:8:10 were mixed in buffer containing 20 mm HEPES pH 7.5, 150 mm NaCl and incubated for 2 hr at 4° C. The Salipro formation was initiated by adding 160 mg/mL equilibrated SM2 biobeads (Bio-Rad) to remove detergents and under constant agitation overnight at 4° C. Subsequently, the sample was incubated for 30 min at 4° C. with 160 mg/mL of equilibrated SM2 biobeads twice (Bio-Rad), to remove residual detergents. The sample was then filtered through a 0.22 μm-pore centrifugal filter and submitted to SEC on a Superose 6 Increase 10/300 column (GE Healthcare) equilibrated with SEC buffer (20 mM HEPES pH7.5, 150 mM NaCl). SEC peak fraction was pooled and concentrated to 2.0 mg/mL and stored at −80° C. for further usage.

To prepare the WT MCT1/BSG-2 in complex with WZHAb10Fab, the fresh WZHAb10Fab (see below) and WT MCT1/BSG-2 embedded in Salipro nanoparticles were incubated for 2 hr on iced water bath with 1.3 molar excess of WZHAb10Fab. The mixtures were concentrated to 0.5-1.0 mL using a 100,000 MWCO Amico centrifugal filter, and then subjected to SEC on a Superose 6 Increase 10/300 column (GE Healthcare) equilibrated with SEC buffer (20 mM HEPES pH7.5, 150 mM NaCl). Fractions from the center of the gel filtration peak were concentrated to 0.7 mg/mL. The final sample was centrifuged at 20,000×g for 5 min at 4° C. to pellet any debris and then the sample was vitrified as quickly as possible as described below.

(4) Antibody Selection and Production

To produce the mouse anti-MCT1/BSG-2 monoclonal antibody WZHAb10, C57BL/6 mice were immunized with 50 μg MCT1/BSG-2 complex reconstituted into Salipro nanoparticle as described above. This initial immunization was followed by 4 boosts, each in 50 μg protein. Around 2000 hybridoma cells were created by fusing SP2/0-Ag14 mouse myeloma cells with splenic B lymphocytes derived from the immunized animal. Culture supernatants were screened with ELISA for reactivity. ELISA screening was carried out in detergent-free conditions using MCT1/BSG-2 embedded in Salipro nanoparticle and captured on MaxiSorp surface plates (Thermofisher). 20 ELISA-positive, immunoblot-negative hybridomas were subcloned by serial dilution three times and their antibodies were purified by affinity chromatography using Protein A Sepharose 4 Fast Flow columns. The eluted antibodies were dialyzed overnight against mAb dialysis buffer (20 mM $Na_3PO_4$ pH 7.5 and 150 mM NaCl) and assayed for binding to MCT1/BSG-2 complex by gel filtration. Five antibodies exhibited strong binding to MCT1/BSG-2, but only one, designated WZHAb10 (subclass IgG2), was proved to inhibit MCT1 transport activity.

The Fab of IgG-WZHAb10 was sequenced as follows: RNA was extracted from hybridoma cells with HiPure RNA Mini Columns (Magen) according to the manufacturer's instructions. NanoDrop and gel electrophoresis were employed to measure the RNA concentration and integrity. cDNA was synthesized from RNA with SMARTScribe Reverse Transcriptase (Takara) with oligo-dT and template switch oligo (TSO) according to the manufacturer's instructions. The resulting cDNA was diluted for amplification. The forward primer was anchored to the TSO and the reverse primers were binding to the constant regions of heavy chain or light chain. The 5' ends of forward primer and reverse primer were tagged with partial P5 and P7 adaptors (Illumina), respectively. Heavy-chain and light-chain fragments were amplified in separate reactions in the first stage PCR.

PCR products were purified with magnetic beads. During the second stage PCR, index primers were attached to both ends of the first stage PCR products to form TruSeq dual index library. The libraries were purified with magnetic beads and quantified by Qubit 4 Fluorometer (Thermo Fisher) and finally sequenced on Illumina MiSeq (pair-end 2×300 bp) following manufacturer's user manual (Illumina). Raw fastq files were first subject to quality assessment. Adapters and bases with poor quality scores (Q value lower than 20) were removed using Trimmomatic (v0.36) to generate clean data (trimmed data). Pandaseq (2.10) was used to merge pair-end read. Merged sequences were processed by IgBLAST software to identify the V(D)J sequences. The reference sequences were obtained in IMGT database (4). The mouse WZHAb10 was humanized using a 'humanized yeast' platform.

To generate WZHAb10Fab, the full-length antibody was digested with 1:100 w/w papain for 5 hr at 37° C. in mAb dialysis buffer (see above) supplemented with 1 mM EDTA, 10 mM L-Cysteine hydrochloride, and 50 mM $Na_3PO_4$ pH 7.5. Following digestion, the papain was inactivated with 30 mM iodoacetamide for 15 min on ice and the digested Fab was submitted to SEC on a Superdex 200 Increase 10/300 column (GE Healthcare) equilibrated with buffer (20 mM HEPES pH7.5, 150 mM NaCl). Purified Fab was used immediately for MCT1/BSG-2 binding experiments, including cryo-EM grid preparation, or else flash frozen by liquid nitrogen and stored at −80° C. for further usage.

Example 3: Monoclonal Antibody WZHAb10 Bound BSG-2 to Inhibit Transport Activities of MCTs 1 and 4

(1) Preparation of Proteoliposomes or Protein-Free Liposomes Encapsulated HPTS proteoliposomes were prepared using the following purified protein samples: WT MCT1, WT MCT1/BSG-2, WT MCT4, WT MCT4/BSG-2, or MCT1/BSG-2 mutational and truncating variants. Lipid mixtures, POPC, POPE, POPG and cholesterol (all lipids were from Avanti) at a 3:1:1:1:1 ratio (w/w) dissolved in chloroform were first dried under an argon stream into lipid film, and then subjected to a vacuum for 16 hr to completely eliminate chloroform. Dried lipids were resuspended by sonication in buffer containing 20 mM Tris pH 8.5 and 150 mM NaCl. 12 mM N-Octyl-β-D-Maltopyranoside (OM, Anatrace) was added and mixed with 10 mg/mL lipid suspension for 2 hours at room temperature. Protein sample purified in DDM was added to the lipid/OM mixture at a protein-to-lipid molar ratio of 1:1000. After 4 hr incubation at room temperature, SM2 biobeads (Bio-Rad) were added to remove detergents by incubating the mixture at 4° C. overnight. Subsequently, the mixture was incubated with SM2 biobeads for 30 min at 4° C. for three additional times to remove residual detergents. The mixture was then loaded to manually packed Sephadex G-50 column (Sephadex G-50 Superfine, Cytiva), which was pre-equilibrated with the reconstitution buffer. Fractions that could be stained by Bradford dye (Bio-Rad) were collected and concentrated using Amicon Ultra centrifugal filter (0.5 mL, 100 kDa cutoff) to a final concentration of 2.5 mg/mL. The protein concentration after reconstitution was measured in the same way as described above, and furtherly confirmed by Coomassie Blue staining and Western Blot.

To load pH-sensitive fluorescent dye, 8-Hydroxypyrene-1,3,6-trisulfonic acid (HPTS, Merck Millipore) into proteoliposomes, proteoliposomes were mixed with 0.1 mM HPTS and sonicated in iced water bath with multiple cycles of 1 min on and 1 min off to prevent overheating. Then, the mixture was extruded (25 times) through a polycarbonate filter with pore size of 0.2 μm, using a lipid extruder (Avanti). After extrusion, the untrapped dye was removed by Sephadex G-50 column, eluted with buffer containing 20 mM Tris pH 8.5 and 150 mM NaCl. The eluted fraction containing HPTS-loaded proteoliposomes was collected and concentrated to 2.0 mg/mL or 2.5 mg/mL. Protein-free liposomes, designated empty liposomes, were prepared in parallel in the same manner in the absence of protein. Freshly-made HPTS-encapsulated proteoliposomes and empty liposomes were used for flux assay within 48 hours.

(2) Fluorescence-Based Flux Assays

All fluorescence-based flux assays were performed at 25° C. HPTS-encapsulated empty liposomes, unless otherwise stated, were executed as negative control in parallel in the same manner as proteoliposomes.

(3) The Substrate Selectivity Assay

The proteoliposomes were reconstituted with WT MCT1, WT MCT1/BSG-2, WT MCT4 or WT MCT4/BSG-2, each at 2.0 mg/mL. The assays were executed with a SpectraMax i3 (Molecular Devices) plate reader, based on a previously published method (5) with modification. Each well of a Nunc MicroWell 96-well plate (Thermofisher Scientific) was first filled with 85 μL of extraliposomal buffer containing 20 mM HEPES pH 7.0 and 150 mM NaCl, followed by a gentle mix of 10 μL of HPTS-loaded proteoliposomes. After incubation for 10 min, the baseline fluorescence $F_{start}$ was recorded every 15 s for 8 cycles with excitation and emission wavelengths of 450 nm and 510 nm, respectively. Then 5 μL test substance with a final concentration of 25 mM was added to initiate H+ influx, and the fluorescent signal F was monitored every 15 s for 60 cycles. After monitoring the flux signal for 15 min, the proteoliposomes were sonicated to allow H+ and test substance to pass through the membrane and reach equilibrium. The final fluorescence value $F_{end}$ was then recorded. The test substances used were: sodium chloride, sodium citrate, sodium D-lactate, sodium L-lactate, or sodium pyruvate. Each test substance was adjusted to pH 7.0 using HCl or NaOH.

(4) H+ Influxes Under Different H+ Gradients

The proteoliposomes were reconstituted with WT MCT1 or WT MCT1/BSG-2, each at 2.0 mg/mL. H+ influx assays were executed in the same procedure as described above for substrate selectivity assay, except for two changes. First, the extraliposomal buffer was replaced by one of the following test buffers including 150 mM NaCl: 20 mM Tris pH 8.5, 20 mM HEPES pH 7.5, 20 mM HEPES pH 7.0, or 20 mM MES pH 6.5. Second, the H+ influx was initiated by 25 mM pyruvate adjusted at the corresponding pH values, after the recording of $F_{start}$.

(5) H+ Influx Under Different Pyruvate or L-Lactate Gradients

To test the influence of pyruvate gradients on H+ influx, proteoliposomes were reconstituted with WT MCT1 or WT MCT1/BSG-2, each at 2.0 mg/mL. The assays were executed in the same procedure as describe above for substrate selectivity assay, except for one change: H+ influx, after the recording of $F_{start}$, was initiated by pyruvate pH 7.0, at each final concentrations of 0 mM, 5 mM, 25 mM, or 100 mM. To test the influence of L-lactate gradients on H+ influx, proteoliposomes were reconstituted with WT MCT4 or WT MCT4/BSG-2. The assays were executed in the same procedure as describe above for pyruvate gradients, except for the replacement of pyruvate by L-lactate pH7.0 at each final concentrations of 0 mM, 5 mM, 25 mM, or 100 mM.

(6) H+-Pyruvate Symport Mediated by MCT1/BSG-2 Mutational Variants

To compare the H+ influxes mediate by WT MCT1 or WT MCT1/BSG-2 to those mediated by MCT1/BSG-2 mutational variants, proteoliposomes were reconstituted with WT MCT1, or WT MCT1/BSG-2, or MCT1/BSG-2 variants, each at 2.0 mg/mL. The assays were executed in the same procedure as described above for substrate selectivity assay, except for one modification: H+ influx was initiated by 25 mM pyruvate pH7.0, after the recording of $F_{start}$.

(7) H+-Pyruvate Symport Mediated by WT MCT1 or WT MCT1/BSG-2 in Presence of WZHAb10, AZD3965 or Both The following stock solutions were prepared for the assays: 200 uM WZHAb10 or IgG negative control each prepared in buffer containing 20 mM Tris pH 8.5, 150 mM NaCl: 20 mM AZD3965 in pure dimethyl sulfoxide (DMSO, Merck Millipore); HPTS-encapsulated proteoliposomes reconstituted with WT MCT1 or WT MCT1/BSG-2, each at 2.5 mg/mL in buffer containing 20 mM Tris pH 8.5 and 150 mM NaCl.

To measure H+-pyruvate symport in presence of WZHAb10, AZD3965 or both, HPTS-encapsulated proteoliposomes at final concentration of 2.0 mg/mL were mixed with WZHAb10 or AZD3965 at final concentrations of 3 μM, or 6 μM, or their combination (3 μM+3 μM, or 6 μM+6 μM), in buffer containing 20 mM Tris pH 8.5 and 150 mM NaCl. The mixture was incubated for 2 hr with gentle rotation at 4° C. After incubation, the mixtures were immediately used for assays, which were executed in the same procedure as described above for assays of H+-pyruvate symport mediated by MCT1/BSG-2 mutational variants. 2.0 mg/mL HPTS-encapsulated proteoliposomes in presence of 6 μM IgG and 0.03% DMSO were used as controls, and executed in parallel in the same manner.

(8) H+-Pyruvate Symport Mediated by MCT1/BSG-2 Mutational and Truncating Variants in Presence of WZHAb10

The following stock solutions were prepared for the assays: 200 uM WZHAb10 or IgG control each prepared in buffer containing 20 mM Tris pH 8.5, 150 mM NaCl; 2.5 mg/mL HPTS-encapsulated proteoliposomes reconstituted with WT MCT1, or MCT1/BSG-2 mutational or truncating variants, respectively, in buffer containing 20 mM Tris pH 8.5 and 150 mM NaCl.

To measure the inhibitory effect of WZHAb10 on H+-pyruvate symport mediated by proteoliposomes, WZHAb10 at final concentration of 6 μM, was mixed with 2.0 mg/mL HPTS-encapsulated proteoliposomes in buffer containing 20 mM Tris pH 8.5 and 150 mM NaCl. The mixture was incubated for 2 hr with gentle rotation at 4° C. After incubation, the mixtures were immediately used for assays, which were executed in the same procedure as described above for assays of H+-pyruvate symport mediated by MCT1/BSG-2 mutational variants. 2.0 mg/mL HPTS-encapsulated proteoliposomes in presence of 6 µM IgG were used as controls, and executed in parallel in the same manner.

(9) Immunofluorescence Staining

The treated cells were cultured on small round cover glasses, fixed with 4% paraformaldehyde, permeabilized with 0.2% Triton X-100, blocked with 5% bovine serum, and treated with mouse Anti-EMMPRIN/CD147 antibody (Santa Cruz), and rabbit anti-MCT4 or MCT1 (Thermofisher Scientific) antibodies overnight at 4° C. After being incubated with the corresponding fluorescence-labeled secondary antibodies (Alexa Fluor 555-labeled goat anti-mouse IgG (H+L), and Alexa Fluor 488-labeled, Goat anti-rabbit IgG (H+L); both from Thermofisher Scientific), the samples were visualized under an OLYMPUS IX83 confocal florescence microscope to assess co-localization of BSG-2 and MCT1 or MCT4.

(10) H+-L-Lactate Symport Mediated by WT MCT4 and WT MCT4/BSG-2 in Presence of WZHAb10

The following stock solutions were prepared for the assays: 200 uM WZHAb10 or IgG control each prepared in buffer containing 20 mM Tris pH 8.5, 150 mM NaCl; 2.5 mg/mL HPTS-encapsulated proteoliposomes reconstituted with WT MCT4, or WT MCT4/BSG-2, respectively, in buffer containing 20 mM Tris pH 8.5 and 150 mM NaCl.

To measure the inhibitory effect of WZHAb10 on H+-L-Lactate symport mediated by proteoliposomes, WZHAb10 at final concentration of 6 µM, was mixed with 2.0 mg/mL HPTS-encapsulated proteoliposomes in buffer containing 20 mM Tris pH 8.5 and 150 mM NaCl. The mixture was incubated for 2 hr with gentle rotation at 4° C. After incubation, the mixtures were immediately used for assays, which were executed in the same procedure as described above for assays of H+-pyruvate symport mediated by MCT1/BSG-2 mutational variants (BSG-2D136A, BSG-2E146A, BSG-2S145A, BSG-2Q195A, BSG-2D194A,), except for one modification: H+ influx was initiated by 25 mM L-Lactate pH7.0, after the recording of $F_{start}$. 2.0 mg/mL HPTS-encapsulated proteoliposomes in presence of 6 µM IgG were used as controls and executed in parallel in the same manner.

(11) Data Analysis

For flux assays, fluorescence data were first normalized to eliminate baseline fluorescence fluctuations using the following equation:

$$F_{normalized} = \frac{F - F_{end}}{F_{start} - F_{end}}$$

Where $F_{normalized}$ is the normalized fluorescence plotted in the flux assay figures, F is measured fluorescence in arbitrary units, $F_{start}$ is the average of measured fluorescence before H+ influx initiated by the addition of monocarboxylate substrates, and $F_{end}$ is the measured end point fluorescence after disruption of proteoliposomes by sonication. Normalizations were performed with Excel (Microsoft).

Prism software (GraphPad) was used to analyze flux assays, cell viabilities, lactate concentrations, and tumor growth. Statistical significance (p<0.05) was assessed using Student's T-test. Error bars represented SD.

Figure 3:
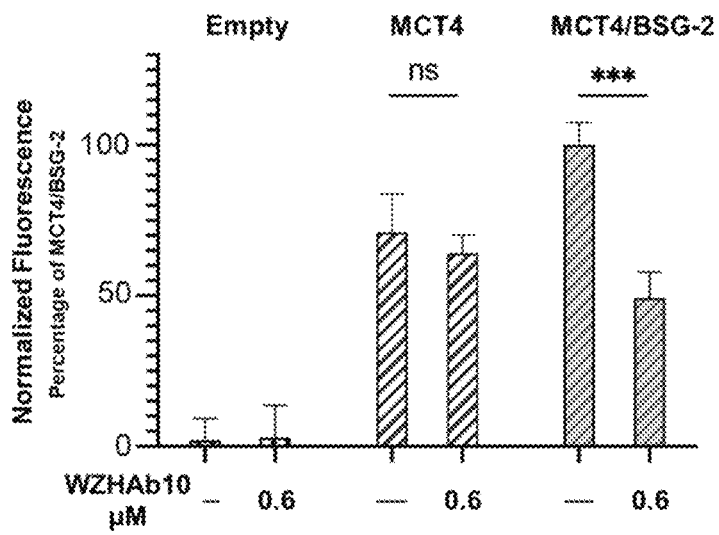
FIG. 3 shows H+ influx mediated by MCT4 and MCT4/BSG-2 in presence of WZHAb10, demonstrating inhibiting efficacy of WZHAb10 on MCT4.

WZHAb10 reduced transport activity of MCT1/BSG-2 and MCT4/BSG-2 by around 75% and 50%, respectively (FIGS. 2-3). Notably, WZHAb10 did not affect transport activity of MCT1 or MCT4 uncoupled to BSG-2, denoting that WZHAb10 allosterically inhibits MCT1 or MCT4 by binding BSG-2.

In order to figure out if WZHAb10 exerts similar inhibitory effects on the transport activity of MCTs to small-molecule inhibitors, the inhibiting efficacy of WZHAb10 and AZD3965 (a potent and selective small-molecule MCT1 inhibitor developed by Astrazeneca, which is in clinical trial (clinicaltrials.gov/ct2/show/NCT01791595)) on MCT1 were compared (FIG. 2), because selective, potent small-molecule inhibitors for MCT4 were not commercially available. Interestingly, WZHAb10 resulted in a similar or even stronger inhibition of MCT1/BSG-2-mediated H+ influx. Whether WZHAb10 and AZD3965 had combinatorial effect on MCT1 inhibition was furtherly investigated. Indeed, the presence of both WZHAb10 and AZD3965 at half concentrations inhibited MCT1/BSG-2-mediated H+ influx as effectively as AZD3965 or WZHAb10 alone did (FIG. 2), suggesting a possibility of exploiting orthosteric and allosteric inhibitors for MCT1/BSG-2 complex.

WZHAb10, acts as efficaciously as other know MCT inhibitors, on the transport activities of MCTs. For comparison, AZD3965, a potent orthosteric inhibitor of MCT1 in clinical trial, was chosen for test. Indeed, WZHAb10, alone and in combination with AZD3965, suppressed transport activity of MCT1/BSG-2, at similar magnitudes as that conferred by AZD3965 (FIG. 2), suggesting allosteric modulation can be explored alone or in combination with orthosteric regulation to intercede in the activities of transporters MCT1, MCT3, and MCT4 that use BSG-2 as their chaperone protein.

Figure 4:
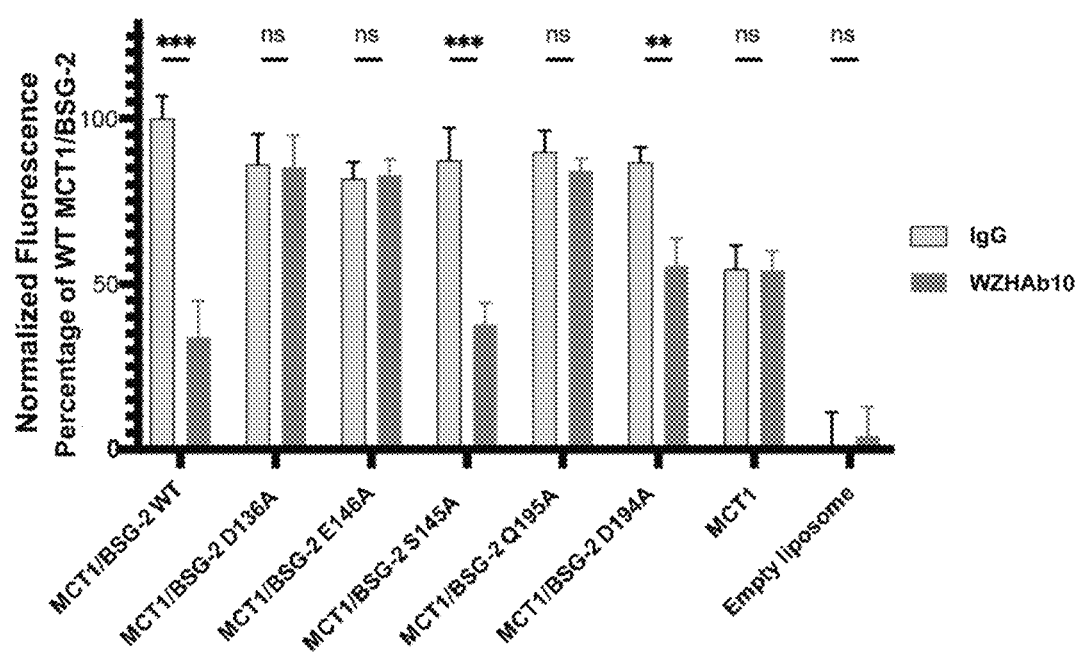
FIG. 4 shows transport activities of MCT1/BSG-2 variants in absence or presence of WZHAb10, in comparison to an IgG control. The transport activities of MCT1/BSG-2 variants were normalized against those of the WT MCT1/BSG-2. All data are mean±SD(n=3). *, $p<0.05$. , $p<0.01$. *, $p<0.001$. ns, not statistically significant.
Figure 5:
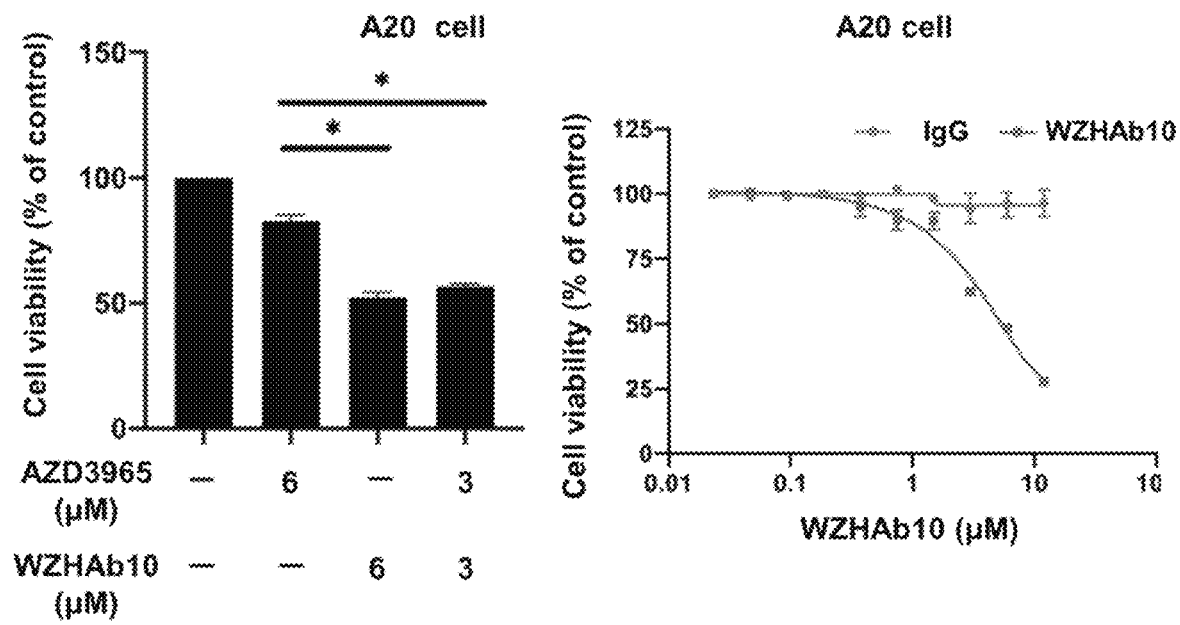
FIG. 5 shows viability of A20 cells in presence of AZD3965 and/or WZHAb10 and IC50 measurement of WZHAb10 to A20 cells
Figure 6:
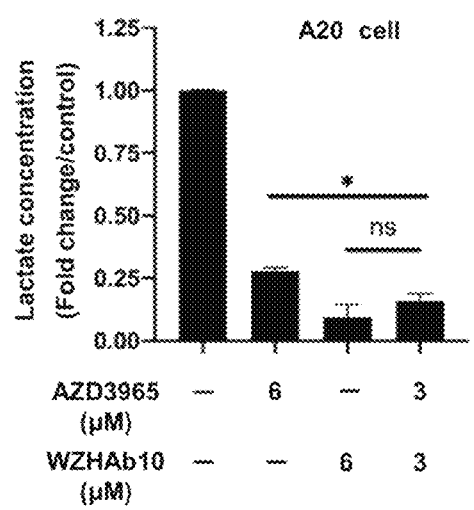
FIG. 6 shows the fold changes of lactate concentration in A20 cells treated with WZHAb10 and/or AZD3965.
Figure 7:
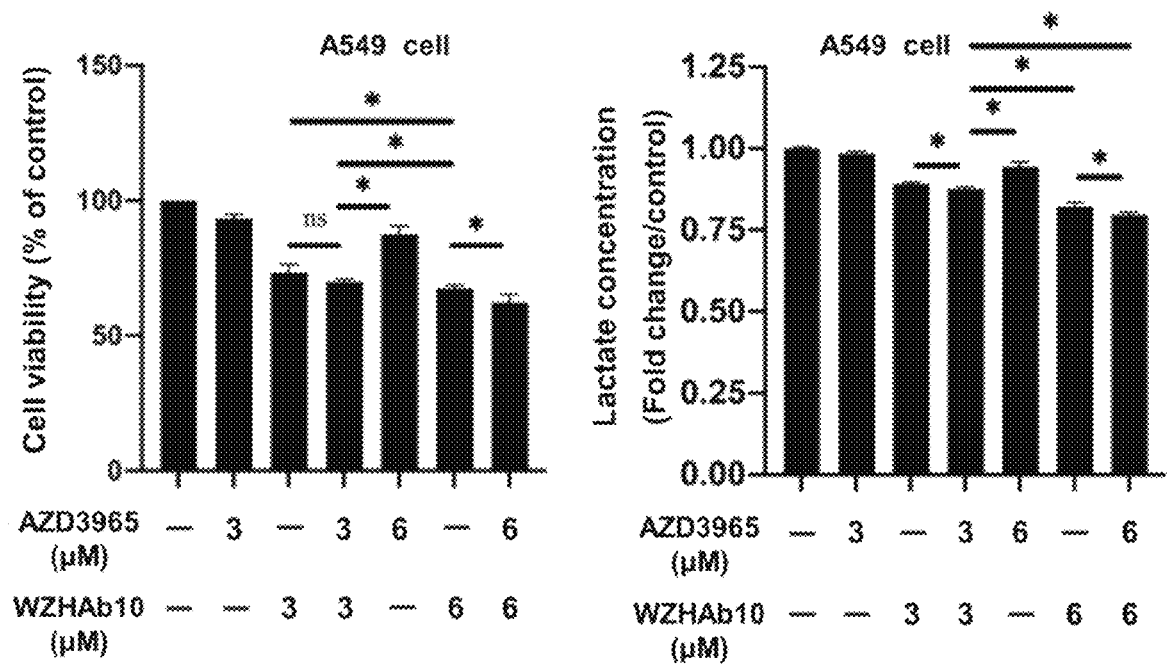
FIG. 7 shows viability of A549 cells in presence of WZHAb10 and/or AZD3965 and the fold change of lactate concentration in culture of A549 cells treated with WZHAb10 and/or AZD3965. All data are mean±SD (n=3). *, $p<0.05$.
Figure 8:
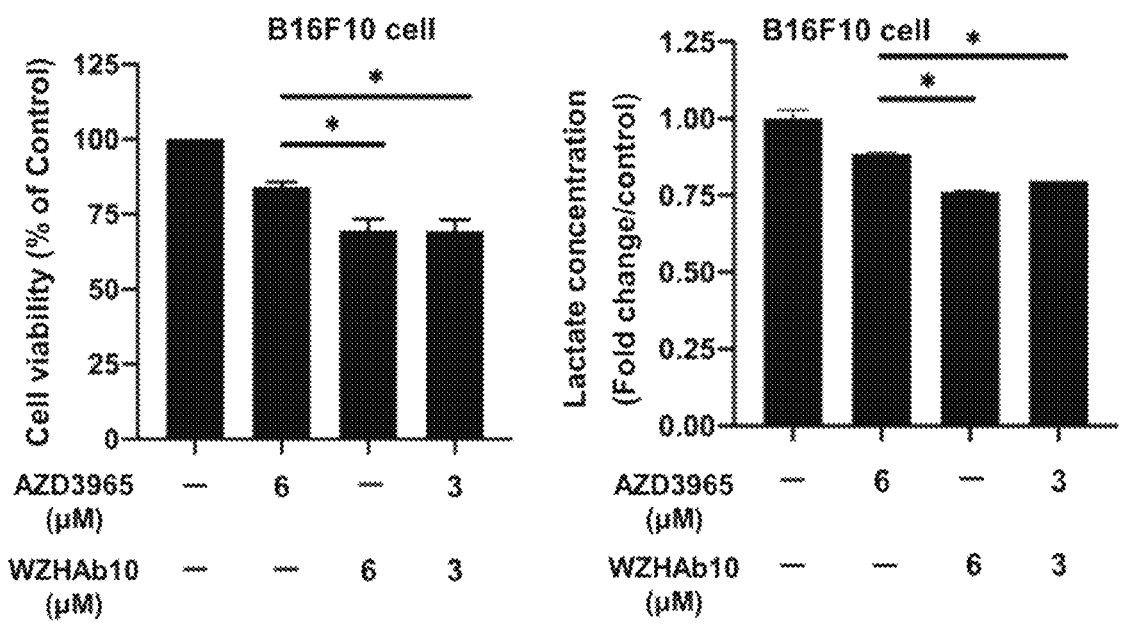
FIG. 8 shows viability of B16F10 cells in presence of AZD3965 and/or WZHAb10 and the fold changes of lactate concentration in cultures of B16F10 cells treated with WZHAb10 and/or AZD3965. *, $p<0.05$.

FIG. 4 shows transport activities of MCT1/BSG-2 variants in absence or presence of WZHAb10, in comparison to an IgG control. The results indicated that the crucial residues of BSG-2 interacting with WZHAb10 could influence its inhibitory activity on the transport activities of MCTs.

The transport activities of MCT1/BSG-2 variants were normalized against those of the WT MCT1/BSG-2. All data are mean±SD (n=3). *, p<0.05. , p<0.01. *, p<0.001. ns, not statistically significant. Intraliposomal buffer (buffer intra a liposome): 150 mM NaCl, 0.1 mM HPTS, 20 mM Tris pH 8.5; extraliposomal buffer: 150 mM NaCl, 25 mM pyruvate, 20 mM HEPES pH 7.0. Empty liposome is negative control.

Example 4: WZHAb10 Inhibited Growth of Cancer Cells In Vitro (1) Cell Culture and Transfection A549 (ATCC number CCL-185), A20 (ATCC number TIB-208), and B16F10 (ATCC number CCL-6475) cells were cultivated in RPMI1640 (Merck Millipore) with 10% fetal bovine serum (FBS, Thermofisher Scientific), penicillin (100 U/ml, Merck Millipore) and streptomycin (100 µg/ml, Merck Millipore). A20 cells were cultured in normoxia (21% $O_2$, 5% $CO_2$ and 37° C.), because the cell viability was observed to dramatically decrease in hypoxia. A549 and B16F10 cells were cultured in both normoxia and hypoxia (1% 02, 5% $CO_2$ and 37° C.). For siRNA transfection, Lipofectamine RNAiMax (Thermofisher Scientific)

was used for A549 cells, and NEPA21 electroporator (NEPA GENE) was employed for A20 cells.

(2) Cell Viability Assay

Cells were seeded in 96-well culture dishes in media (For A20 cells, 3,000 cells per well; For A549 cells and B16F10 cells, 1,500 cells per well). A20 cells were seeded and treated with indicated concentration of AZD3965 and/or WZHAb10 in complete medium for 72 hours. IgG and DMSO group were set as control. Then cell viability was determined with CCK8 kit in SpectraMax i3 (Molecular Devices). For A549 cells and B16F10 cells, cells were incubated overnight to adhere and were treated as indicated in normoxia or hypoxia for 72 hours before cell viability was measured.

(3) Measurement of Lactate Concentration

A20 cells were seeded and treated with indicated concentrations of AZD3965 and/or WZHAb10 in complete medium for 72 hours. IgG and DMSO group were set as control. The lactate concentration was measured with Lactate Colorimetric/Fluorometric Assay Kit (BioVision Catalog #K607-100) in SpectraMax 13 (Molecular Devices). For A549 cells and B16F10 cells, cells were incubated overnight to adhere and were treated as indicated in normoxia or hypoxia for 72 hours before lactate concentration was determined.

WZHAb10 suppressed cell proliferation of A20 lymphoma cells, A549 non-small-cell lung (NSCL) carcinoma cells, and B16F10 melanoma cells (FIGS. 5-8). And WZHAb10 exhibited the additive effect with AZD3965 in low micromolar range, suggesting a combinatory treatment using MCT small-molecule inhibitors and MCT/BSG antibodies for cancer cells. Different cancer cells show varied expression levels of MCT1 and MCT4 in normoxia and hypoxia conditions. Therefore, the reduction of lactate concentrations varied in culture medium, which might corroborate with correspondently inhibited transport activities of MCT1 in presence of AZD3965 or MCTs in complexes with BSG in presence of WZHAb10, or their combination. Consistently, half concentrations of WZHAb10 and AZD3965, when combined together, displayed different inhibitory effect on cancer cell growth, suggesting varied molar ratio combination of small-molecule and biologic inhibitors for effective cancer treatments under normoxia and hypoxia conditions.

If WZHAb10 suppresses tumor survival in vitro and in vivo was investigated, after seeing allosteric modulation of the antibody on mMCT1 and mMCT4. Glycolytic activity is high for murine A20 lymphoma cells at normoxia (45), and for human A549 non-small-cell lung (NSCL) carcinoma cells and murine B16F10 melanoma cells at hypoxia. As expected, WZHAb10 suppressed cell survival and lactate transport of A20 cells at normoxia (FIGS. 5-6), and of A549 cells (FIG. 7) and B16F10 cells (FIG. 8) at hypoxia, respectively.

Figure 11:
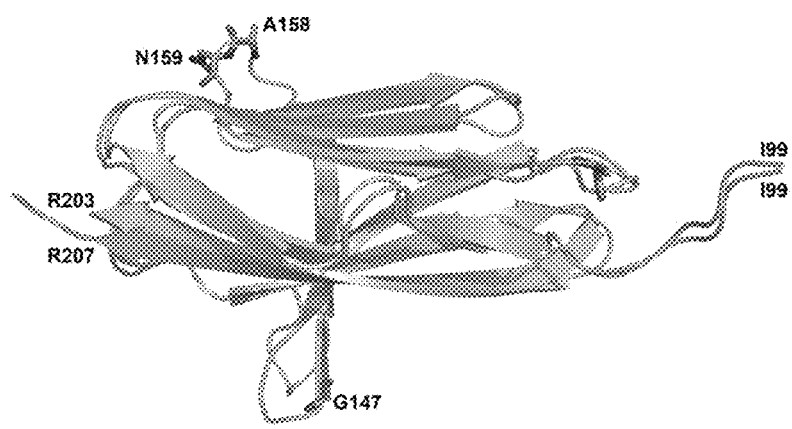
FIG. 11 shows superposition of the Ig2 domains of mBSG-2 and hBSG-2 to indicate the structural similarity between two BSG-2. hBSG-2 is absent of equivalent amino acid residues at G147, A158 and N159 of mBSG-2.

The suppressed survival of these human (A549) and murine (A20 and B16F10) cancer cells conferred by WZHAb10 was concordant with the high structural similarity of extracellular Ig2 domains of human and murine BSG-2s, to which WZHAb10 is tightly bound (FIG. 11), suggesting a common modulation mechanism of WZHAb10 on human and mouse MCT/BSG-2 transporter complexes such as MCT1/BSG-2, MCT4/BSG-2, and MCT3/BSG-2.

Figure 9:
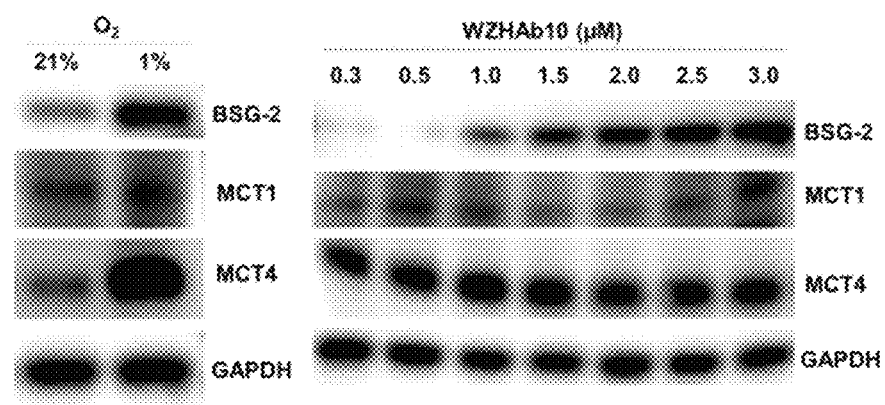
FIG. 9 shows expression of BSG-2, MCT1 and MCT4 of A549 cells cultured in normoxia (02, 21%) and hypoxia (02, 1%) and expression of BSG-2, MCT1 and MCT4 of A549 cells in presence of different concentration of WZHAb10.
Figure 10:
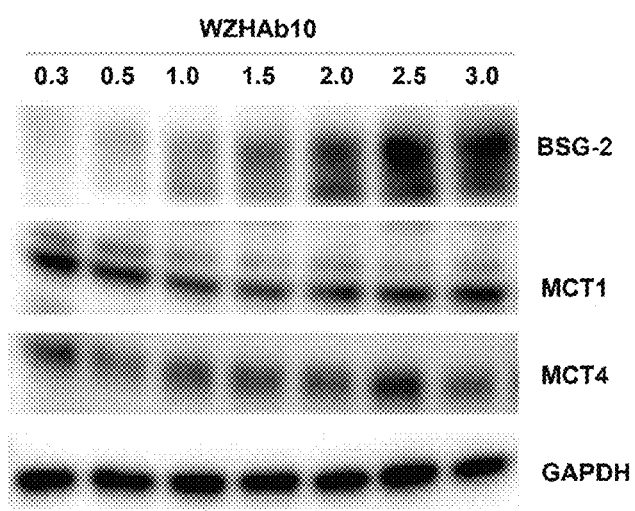
FIG. 10 shows expression of BSG-2, MCT1 and MCT4 of A20 cells in presence of different concentration of WZHAb10.

Although WZHAb10 displayed a similar efficacy to AZD3965 on inhibiting activity of mMCT1 at molecular level (FIG. 2), it elicited a stronger suppression than AZD3965, on the survival and lactate transport of cancer cells (FIGS. 5-8), indicating WZHAb10 inhibited activities of multiple MCTs of cells. Indeed, MCT4 was expressed in A20 and A549 cells (FIGS. 9-10). Furthermore, the combination of allosteric WZHAb10 and orthosteric AZD3965 resulted in additive suppression of cancer cell growth and lactate flux (FIGS. 5-8), thus providing a potential alternative approach to the treatment of glycolytic cancer cells.

Example 5: WZHAb10 Inhibited Growth of Cancer Cells In Vivo Xenograft Models

Three- to four-week-old male or female BALB/c nude mice were purchased from Animal Center of Guangxi Medical University. A20 cells and A549 cells were suspended in complete medium. 100 µL cells (1×10$^6$ cells/site) were then injected subcutaneously into the flank region of the mice. After one week, mice (6-8 per group) were treated intraperitoneally with WZHAb10 (5 mg/Kg) every other day, suspended in PBS. IgG was used as control (vehicle). Tumor volume was measured from digital caliper by using the formula: Volume (mm$^3$)=(length×width$^2$)/2.

Figure 12:
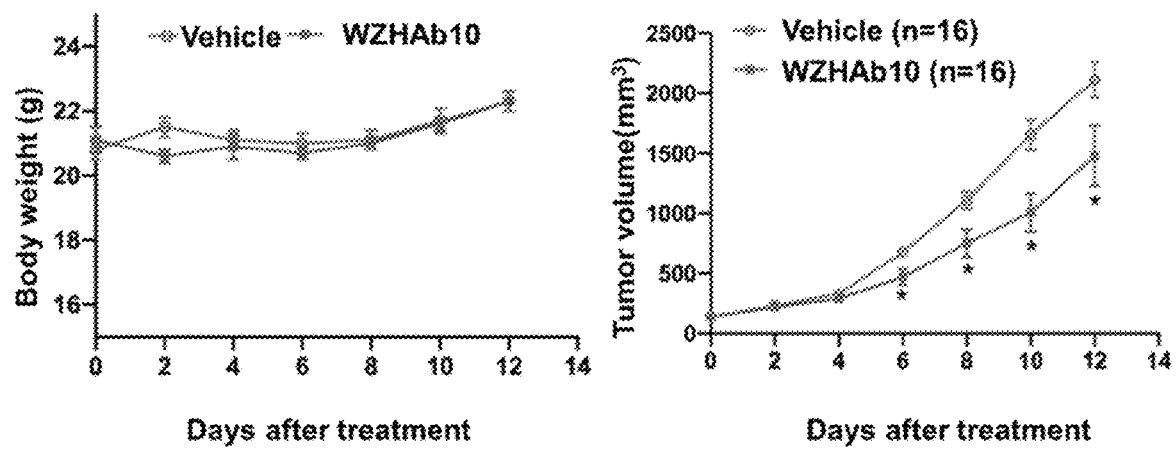
FIG. 12 shows change of body weight of mice during the WZHAb10 treatment in A20 tumor mice and WZHAb10 inhibits the growth of A20 tumor in mice. Mice tumor model were treated upon appearance of tumors with 5 mg/kg WZHAb10 or IgG (i.p.) every other day.
Figure 13:
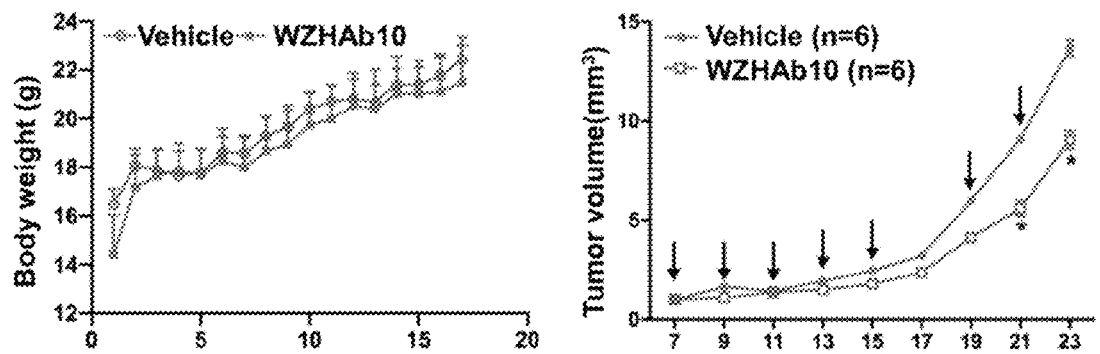
FIG. 13 shows change of body weight of mice during the WZHAb10 treatment in A549 xenograft mice and WZHAb10 inhibits the growth of A549 xenograft tumor in mice. Mice tumor model were treated upon appearance of tumors with 5 mg/kg WZHAb 10 or IgG (i.p.) every other day.

The present disclosure further examined the anti-tumor efficacy of WZHAb10 on A20(mouse tumor) and A549 (human tumor) xenografts of nude mice. The administration of WZHAb10 (5 mg/kg, ip) evidently suppressed tumor growth while elicited little effect on body weights during treatment (FIGS. 12, 13).

Figure 14:
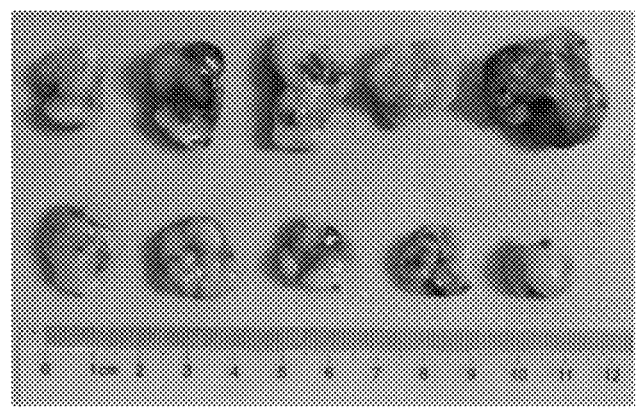
FIG. 14 shows appearance of xenograft A549 tumors at the end of the treatment course with IgG or WZHAb10 (5 mg/kg).

FIG. 14 shows appearance of xenograft A549 tumors at the end of the treatment course with IgG or WZHAb10 (5 mg/kg). WZHAb10 treatment was not associated with any obvious toxicity.

Example 6: The Combined WZHAb10 and Anti PD1 Antibody Show Higher Anti-Tumor Efficacy than these Antibodies Alone Ex Vivo NSCLC Model Non-small cell lung cancer (NSCLC) accounts for ~85% of all lung cancers and is commonly diagnosed in advanced stage. Several anti PD-L1 and anti PD1 antibodies have been approved for treatment of high PD-L1 expression metastatic NSCLC patients. Nonetheless, majority of NSCLC patients are resistant or acquire resistance to the immunotherapy. To investigate if the prevention of lactate release into TME by blocking both MCTs 1 and 4 of cancer cells can improve the activities of effector T cells and checkpoint therapies, three patient-derived organoids (PDO) were used to investigate the combined anti-tumor effect of WZHAb10 and pembrolizumab, the anti PD1 antibody.

(1) PDO Culture

All procedures performed involving human participants were approved by the Ethics Committee of Shanghai Jiao Tong University School of Medicine and were in accordance with the ethical standards of Helsinki Declaration (as revised in 2013). All the donors signed an informed consent form. Freshly excised tumor samples from patients were kept in MACS tissue storage solution (Miltenyi) at 4° C. upon harvest. Tumor tissues were minced into small pieces on ice, then incubated with 0.001% DNase (Sigma-Aldrich, MO, USA), 1 mg/mL collagenase/dispase (Roche, IN, USA), 200 U/mL penicillin, 200 mg/mL streptomycin, and 0.5 mg/mL amphotericin B (2% antibiotics, Sigma) in DMEM/F12 medium (Thermofisher) at 37° C. for three hours with gentle agitation and intermittent resuspension. Thereafter, the digested tissue suspension was repeatedly triturated via pipetting and passed through a 70 μm filter. The strained suspension was centrifuged at 112×g for three minutes, and red blood cells were lysed using lysis buffer (00443357, Thermofisher) for five minutes. The pellet was resuspended in 100 μL serum-free medium (SFM, Thermofisher) supplemented with 20 ng/mL bFGF (Thermofisher), 50 ng/mL human EGF (Thermofisher), N2 (Thermofisher), B27 (Thermofisher), 10 μM ROCK inhibitor (Enzo Life Sciences), and 1% penicillin-streptomycin (Thermofisher). Thereafter, 200 μL Matrigel (Corning) was added to 100 μL of the cell suspension for establishing organoids, and the resulting suspension was allowed to solidify on prewarmed 6-well culture plates (Corning) at 37° C. for 30 minutes. After gelation, 3 mL SFM was added to the well. The medium was changed every four days. Organoids were passaged every two weeks with the ratio of 1:2 or 1:3. For organoid passaging, organoids were firstly harvested by incubating with cold PBS for one hour at 4° C. and dissociated using 1× TrypLe (Thermofisher). The dissociated organoids were then mixed in SFM+ Matrigel (1:3 ratio) and reseeded in a Petri dish, followed by the addition of medium after gelling. Early passage organoids (<3 passages) were frozen in liquid nitrogen for further investigation.

(2) Organoid Drug Response Assay

The organoids cultured over two weeks were harvested and dissociated using 1× TrypLe (Thermofisher). The dissociated organoids were mixed in SFM+ Matrigel (1:3 ratio) and seeded onto 384 well white plates. After gelation, 30 μL SFM was added to each well. The organoids were cultured for 48 hours. The average diameter of organoids was set at 50 μm as the minimum requirement for drug screening.

Figure 15A:
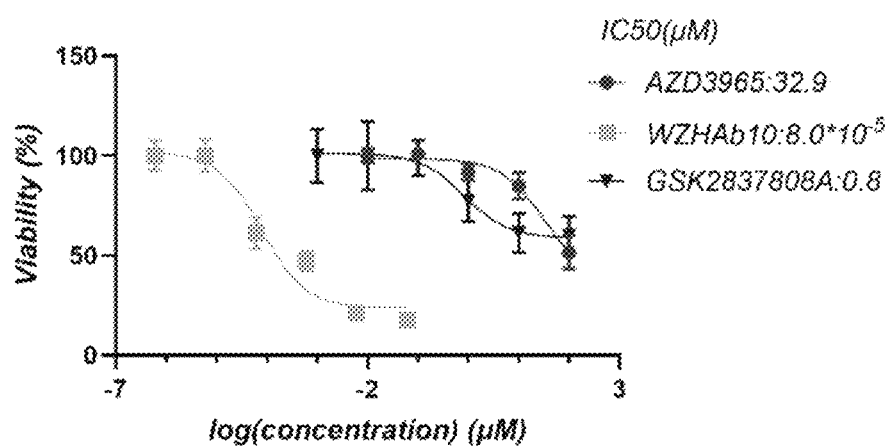
FIG. 15A shows dose-response curves generated from patient 1-derived NSCLC organoid treated with AZD3965, WZHAb10, or GSK2837808A. The viability was measured by a CellTiter-Glo 3D Cell Viability assay. Each assay was run in triplicate for each individual organoid line.
Figure 15B:
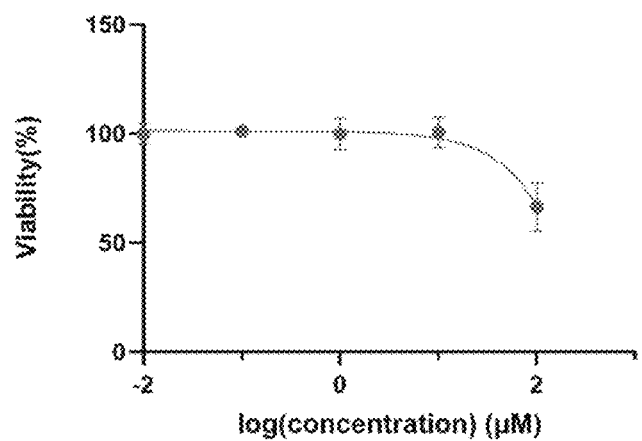
FIG. 15B shows dose-response curve of patient 1's PBMC in presence of AZD3965.
Figure 15C:
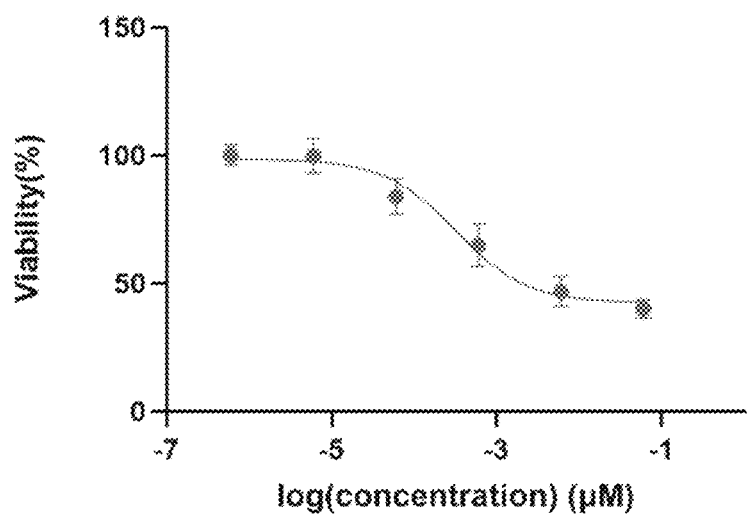
FIG. 15C shows dose-response curve of patient 1's PBMC in presence of WZHAb10.
Figure 15D:
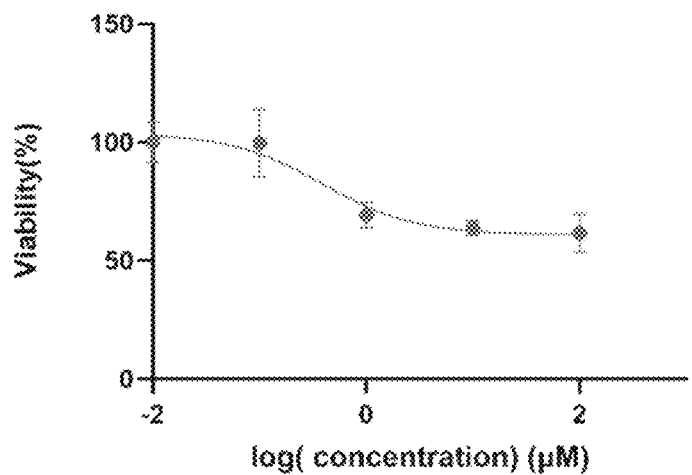
FIG. 15D shows dose-response curve of patient 1's PBMC in presence of GSK2837808A.
Figure 16A:
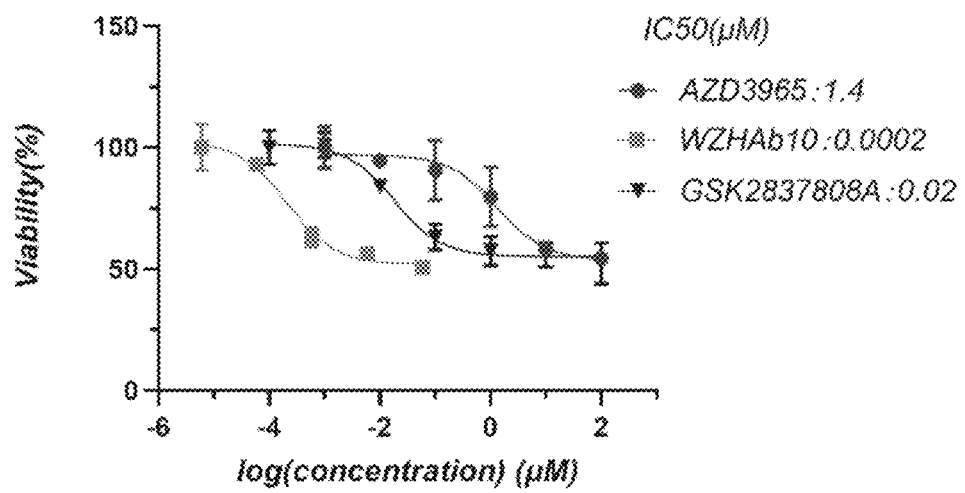
FIG. 16A shows dose-response curves generated from patient 2-derived NSCLC organoid treated with AZD3965, WZHAb10, or GSK2837808A. The viability was measured by a CellTiter-Glo 3D Cell Viability assay. Each assay was run in triplicate for each individual organoid line.
Figure 16B:
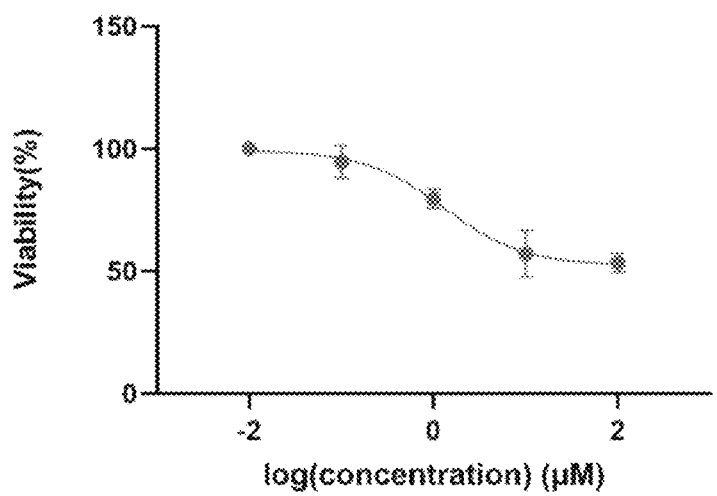
FIG. 16B shows dose-response curve of patient 2's PBMC in presence of AZD3965.
Figure 16C:
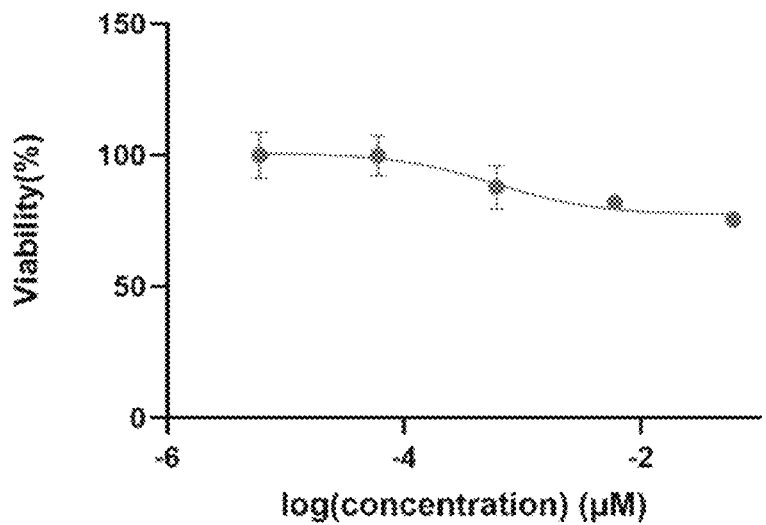
FIG. 16C shows dose-response curve of patient 2's PBMC in presence of WZHAb10.
Figure 16D:
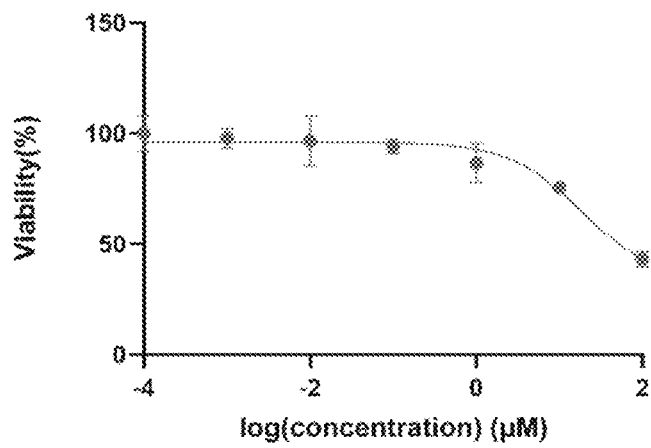
FIG. 16D shows dose-response curve of patient 2's PBMC in presence of GSK2837808A.
Figure 17A:
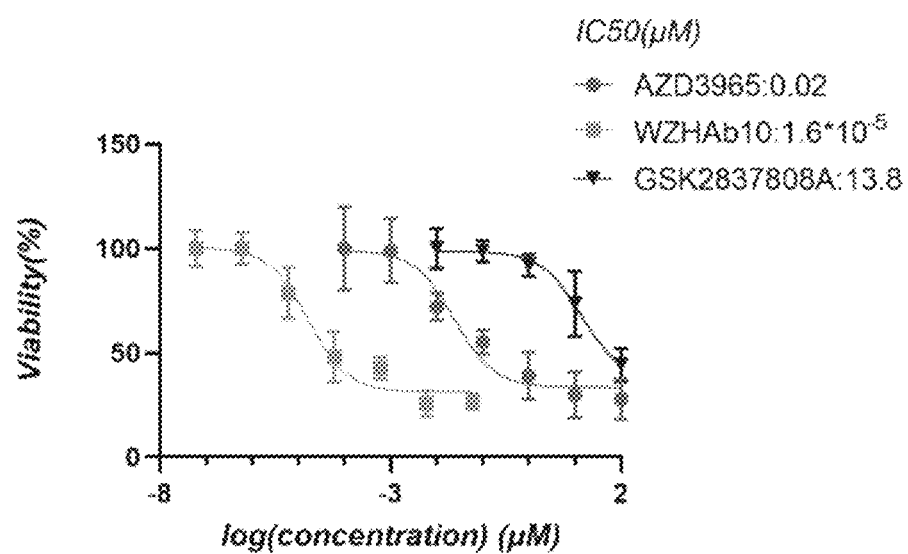
FIG. 17A shows dose-response curves generated from patient 3-derived NSCLC organoid treated with AZD3965, WZHAb10, or GSK2837808A. The viability was measured by a CellTiter-Glo 3D Cell Viability assay. Each assay was run in triplicate for each individual organoid line.
Figure 17B:
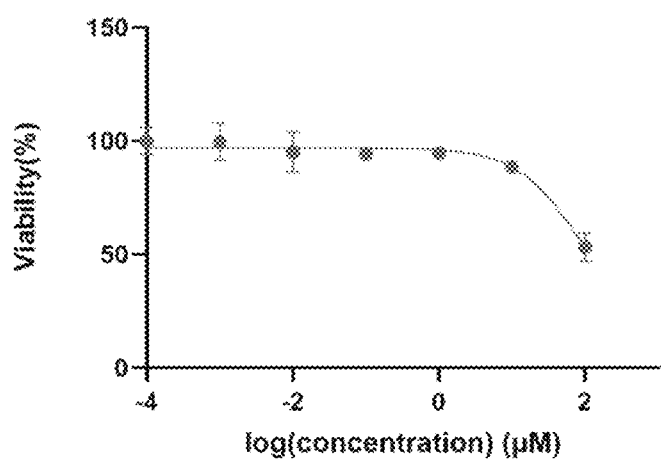
FIG. 17B shows dose-response curve of patient 3's PBMC in presence of AZD3965.
Figure 17C:
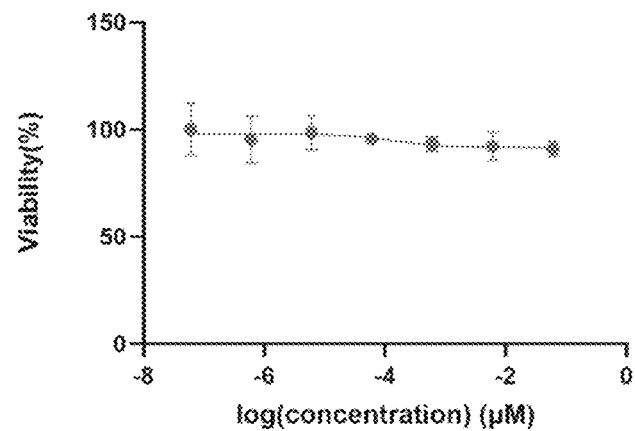
FIG. 17C shows dose-response curve of patient 3's PBMC in presence of WZHAb10.
Figure 17D:
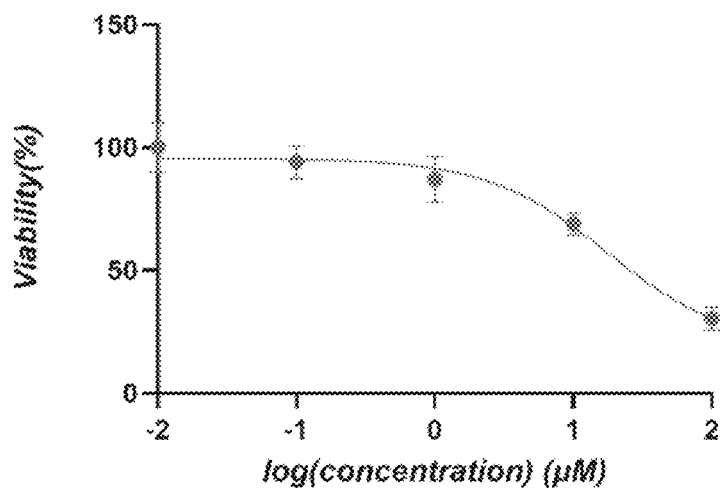
FIG. 17D shows dose-response curve of patient 3's PBMC in presence of GSK2837808A.

Thereafter, a dilution series of each compounds (AZD3965, a MCT1 inhibitor, in 0.001, 0.01, 0.1, 1, 10, 100 M; GSK2837808A (CAS NO. 1445879-21-9), a LDHA inhibitor, in 0.0001, 0.001, 0.01, 0.1, 1, 10, 100 μM) or WZHAb10 (in 0.000006, 0.00006, 0.0006, 0.006, 0.06 μM) was dispensed, and cell viability (FIGS. 15A, 16A and 17A) was assayed using CellTiter-Glo (Promega) after three days of drug incubation. The plates were agitated for 30 minutes at room temperature (10° C.-30° C.) prior to measuring luminescence. As expected, treatment with single agent exerted a moderate anti-proliferative effect across all models, although the magnitude of the response varied between patients. These results are consistent with those observed in xenograft models (FIG. 12-14), suggesting the robustness of blocking lactate metabolism in cancer treatment.

Figure 18:
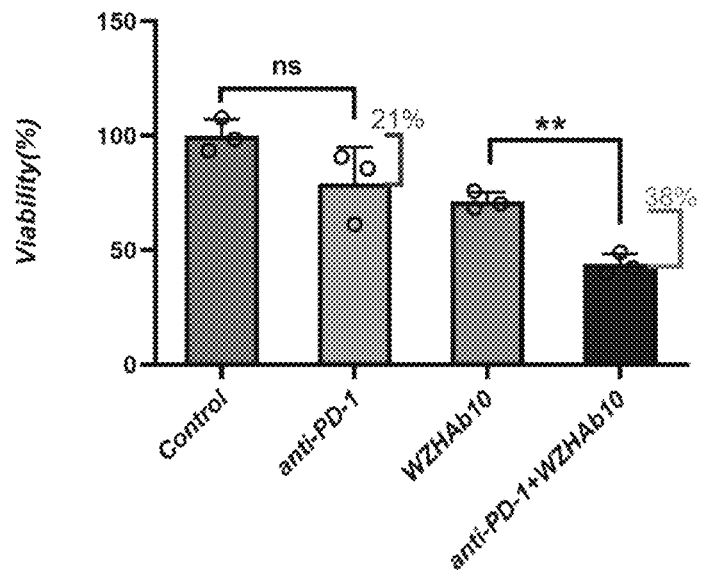
FIG. 18 shows cell viability assay of NSCLC organoids derived from patient 1 that is cocultured with the patient 1's PBMC and treated with either pembrolizumab, WZHAb10, or their combinations. *, $p<0.05$. **, $p<0.01$. ns, not statistically significant.
Figure 19:
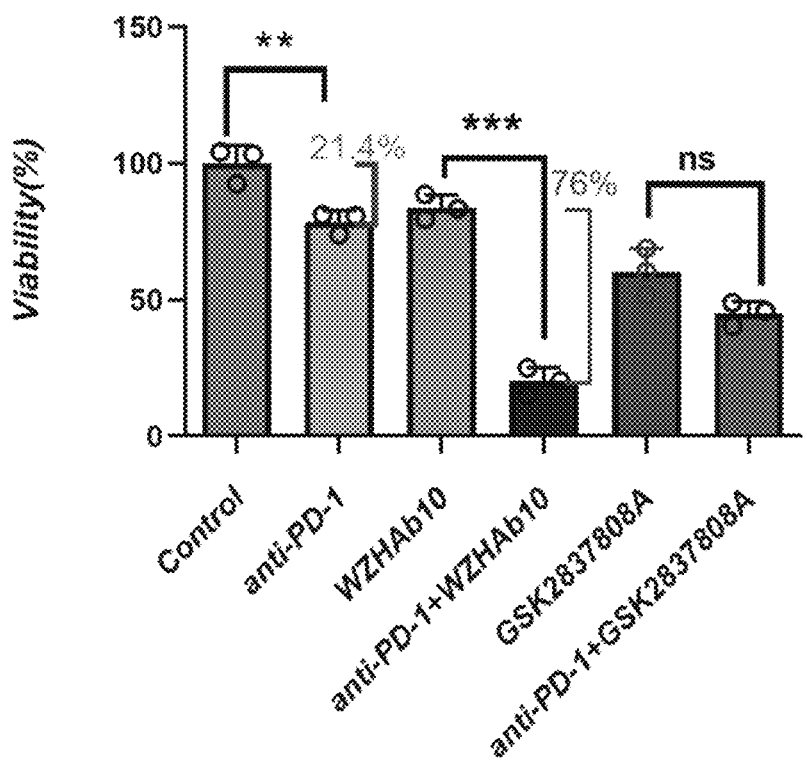
FIG. 19 shows cell viability assay of NSCLC organoids derived from patient 2 that is cocultured with the patient 2's PBMC and treated with either pembrolizumab, GSK2837808A, WZHAb10, or their combinations.
Figure 20:
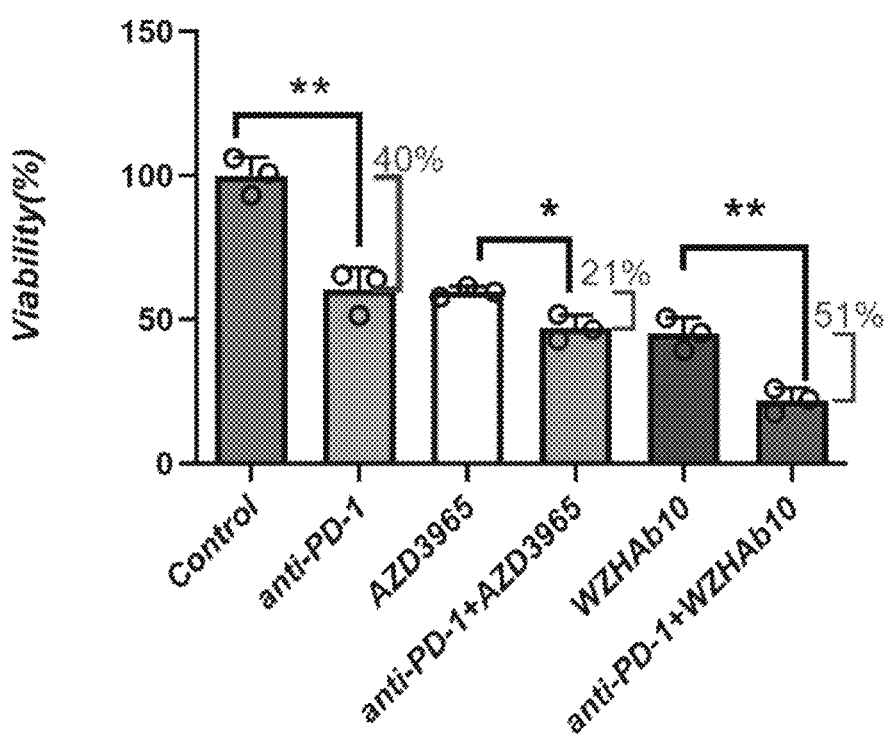
FIG. 20 shows cell viability assay of NSCLC organoids derived from patient 3 that is cocultured with the patient 3's PBMC and treated with either pembrolizumab, AZD3965, WZHAb10, or their combinations.

To investigate if prevention of lactate release into TME of cancer cells improves immune checkpoint blockade therapy, the toxicities of AZD3965, GSK2837808A and WZHAb10 on peripheral blood mononuclear cells (PBMC) obtained from same patients (FIGS. 15 B-D, 16 B-D, 17 B-D) were assayed, it found that AZD3965 at 0.1 μM, GSK2837808A at 1 μM, and WZHAb10 at 0.0006 μM elicited little effects on T cell growth for these patients. Then, treating organoids in presence of 5 μg/mL pembrolizumab, in combination with either of these agents (AZD3965 at 0.1 μM, GSK2837808A at 1 μM, and WZHAb10 at 0.0006 μM) and each PBMC (FIGS. 18, 19 and 20). IgG was used as control in FIG. 18, IgG and/or vehicle were used as control in FIGS. 19-20.

In all cases, the combination of WZHAb10 and pembrolizumab indicates much stronger anti-proliferative effect across all models than pembrolizumab alone does, suggesting WZHAb10 improves immune checkpoint blockade therapy by preventing lactate release into TME of cancer cells.

SEQUENCE LISTING

```
Sequence total quantity: 26
SEQ ID NO: 1           moltype = AA  length = 11
FEATURE                Location/Qualifiers
VARIANT                6
                       note = The X at location 6 stands for any amino acid
VARIANT                7
                       note = The X at location 7 stands for any amino acid
source                 1..11
                       mol_type = protein
                       organism = synthetic construct
SEQUENCE: 1
GYTFTXXWIH W                                                                  11

SEQ ID NO: 2           moltype = AA  length = 19
FEATURE                Location/Qualifiers
VARIANT                8
                       note = The X at location 8 stands for any amino acid
VARIANT                12
                       note = The X at location 12 stands for any amino acid
source                 1..19
                       mol_type = protein
                       organism = synthetic construct
SEQUENCE: 2
MGMIHPNXGS IXYNEKFKT                                                          19

SEQ ID NO: 3           moltype = AA  length = 12
FEATURE                Location/Qualifiers
VARIANT                3
                       note = The X at location 3 stands for any amino acid
VARIANT                6
                       note = The X at location 6 stands for any amino acid
VARIANT                8
                       note = The X at location 8 stands for any amino acid
```

-continued

```
VARIANT               11
                      note = The X at location 11 stands for any amino acid
source                1..12
                      mol_type = protein
                      organism = synthetic construct
VARIANT               10
                      note = The X at location 10 stands for any amino acid
SEQUENCE: 3
CAXVGXGXLX XW                                                              12

SEQ ID NO: 4          moltype = AA  length = 13
FEATURE               Location/Qualifiers
VARIANT               9
                      note = The X at location 9 stands for any amino acid
VARIANT               10
                      note = The X at location 10 stands for any amino acid
source                1..13
                      mol_type = protein
                      organism = synthetic construct
SEQUENCE: 4
CRASQSISXX LHW                                                             13

SEQ ID NO: 5          moltype =    length =
SEQUENCE: 5
000

SEQ ID NO: 6          moltype = AA  length = 9
FEATURE               Location/Qualifiers
VARIANT               4
                      note = The X at location 4 stands for any amino acid
VARIANT               5
                      note = The X at location 5 stands for any amino acid
source                1..9
                      mol_type = protein
                      organism = synthetic construct
VARIANT               6
                      note = The X at location 6 stands for any amino acid
SEQUENCE: 6
QNGXXXPYT                                                                  9

SEQ ID NO: 7          moltype = AA  length = 11
FEATURE               Location/Qualifiers
source                1..11
                      mol_type = protein
                      organism = synthetic construct
SEQUENCE: 7
GYTFTNYWIH W                                                               11

SEQ ID NO: 8          moltype = AA  length = 19
FEATURE               Location/Qualifiers
source                1..19
                      mol_type = protein
                      organism = synthetic construct
SEQUENCE: 8
MGMIHPNSGS INYNEKFKT                                                       19

SEQ ID NO: 9          moltype = AA  length = 12
FEATURE               Location/Qualifiers
source                1..12
                      mol_type = protein
                      organism = synthetic construct
SEQUENCE: 9
CARVGSGSLD YW                                                              12

SEQ ID NO: 10         moltype = AA  length = 13
FEATURE               Location/Qualifiers
source                1..13
                      mol_type = protein
                      organism = synthetic construct
SEQUENCE: 10
CRASQSISDY LHW                                                             13

SEQ ID NO: 11         moltype = AA  length = 8
FEATURE               Location/Qualifiers
source                1..8
                      mol_type = protein
                      organism = synthetic construct
SEQUENCE: 11
KYVSQSIS                                                                   8
```

```
SEQ ID NO: 12            moltype = AA   length = 9
FEATURE                  Location/Qualifiers
source                   1..9
                         mol_type = protein
                         organism = synthetic construct
SEQUENCE: 12
QNGEEAPYT                                                                 9

SEQ ID NO: 13            moltype = AA   length = 117
FEATURE                  Location/Qualifiers
source                   1..117
                         mol_type = protein
                         organism = synthetic construct
SEQUENCE: 13
QVQLVQSGAE VKKPGASVKV SCKASGYTFT NYWIHWVRQA PGQGLEWMGM IHPNSGSINY        60
NEKFKTRVTM TRDTSTSTVY MELSSLRSED TAVYYCARVG SGSLDYWGQG TLVTVSS          117

SEQ ID NO: 14            moltype = AA   length = 107
FEATURE                  Location/Qualifiers
source                   1..107
                         mol_type = protein
                         organism = synthetic construct
SEQUENCE: 14
EIVLTQSPAT LSLSPGERAT LSCRASQSIS DYLHWYQQKP GQAPRLLIKY VSQSISGIPA        60
RFSGSGSGTY FTLTISSLEP EDVAVYYCQN GEEAPYTFGQ GTKLEIK                     107

SEQ ID NO: 15            moltype = AA   length = 329
FEATURE                  Location/Qualifiers
source                   1..329
                         mol_type = protein
                         organism = synthetic construct
SEQUENCE: 15
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELLGG       120
PSVFLFPPKP KDTLMISRTP EVTCVVVDVS HEDPEVKFNW YVDGVEVHNA KTKPREEQYN       180
STYRVVSVLT VLHQDWLNGK EYKCKVSNKA LPAPIEKTIS KAKGQPREPQ VYTLPPSREE       240
MTKNQVSLTC LVKGFYPSDI AVEWESNGQP ENNYKTTPPV LDSDGSFFLY SKLTVDKSRW       300
QQGNVFSCSV MHEALHNHYT QKSLSLSPG                                        329

SEQ ID NO: 16            moltype = AA   length = 107
FEATURE                  Location/Qualifiers
source                   1..107
                         mol_type = protein
                         organism = synthetic construct
SEQUENCE: 16
RTVAAPSVFI FPPSDEQLKS GTASVVCLLN NFYPREAKVQ WKVDNALQSG NSQESVTEQD        60
SKDSTYSLSS TLTLSKADYE KHKVYACEVT HQGLSSPVTK SFNRGEC                    107

SEQ ID NO: 17            moltype = AA   length = 446
FEATURE                  Location/Qualifiers
source                   1..446
                         mol_type = protein
                         organism = synthetic construct
SEQUENCE: 17
QVQLVQSGAE VKKPGASVKV SCKASGYTFT NYWIHWVRQA PGQGLEWMGM IHPNSGSINY        60
NEKFKTRVTM TRDTSTSTVY MELSSLRSED TAVYYCARVG SGSLDYWGQG TLVTVSSAST       120
KGPSVFPLAP SSKSTSGGTA ALGCLVKDYF PEPVTVSWNS GALTSGVHTF PAVLQSSGLY       180
SLSSVVTVPS SSLGTQTYIC NVNHKPSNTK VDKKVEPKSC DKTHTCPPCP APELLGGPSV       240
FLFPPKPKDT LMISRTPEVT CVVVDVSHED PEVKFNWYVD GVEVHNAKTK PREEQYNSTY       300
RVVSVLTVLH QDWLNGKEYK CKVSNKALPA PIEKTISKAK GQPREPQVYT LPPSREEMTK       360
NQVSLTCLVK GFYPSDIAVE WESNGQPENN YKTTPPVLDS DGSFFLYSKL TVDKSRWQQG       420
NVFSCSVMHE ALHNHYTQKS LSLSPG                                           446

SEQ ID NO: 18            moltype = AA   length = 214
FEATURE                  Location/Qualifiers
source                   1..214
                         mol_type = protein
                         organism = synthetic construct
SEQUENCE: 18
EIVLTQSPAT LSLSPGERAT LSCRASQSIS DYLHWYQQKP GQAPRLLIKY VSQSISGIPA        60
RFSGSGSGTY FTLTISSLEP EDVAVYYCQN GEEAPYTFGQ GTKLEIKRTV AAPSVFIFPP       120
SDEQLKSGTA SVVCLLNNFY PREAKVQWKV DNALQSGNSQ ESVTEQDSKD STYSLSSTLT       180
LSKADYEKHK VYACEVTHQG LSSPVTKSFN RGEC                                   214

SEQ ID NO: 19            moltype = AA   length = 171
FEATURE                  Location/Qualifiers
source                   1..171
                         mol_type = protein
```

```
                    organism = synthetic construct
SEQUENCE: 19
IQLHGPPRVK AVKSSEHINE GETAMLVCKS ESVPPVTDWA WYKITDSEDK ALMNGSESRF     60
FVSSSQGRSE LHIENLNMEA DPGQYRCNGT SSKGSDQAII TLRVRSHLAA LWPFLGIVAE    120
VLVLVTIIFI YEKRRKPEDV LDDDDAGSAP LKSSGQHQND KGKNVRQRNS S            171

SEQ ID NO: 20           moltype = AA   length = 107
FEATURE                 Location/Qualifiers
source                  1..107
                        mol_type = protein
                        organism = synthetic construct
SEQUENCE: 20
IQLHGPPRVK AVKSSEHINE GETAMLVCKS ESVPPVTDWA WYKITDSEDK ALMNGSESRF     60
FVSSSQGRSE LHIENLNMEA DPGQYRCNGT SSKGSDQAII TLRVRSH                 107

SEQ ID NO: 21           moltype = AA   length = 166
FEATURE                 Location/Qualifiers
source                  1..166
                        mol_type = protein
                        organism = synthetic construct
SEQUENCE: 21
VSIEVEPQVV AYKKSEHGNE GDVGVLTCKS PSYPPVDHWA WYKSGQTVPL ESSAGIYNIS     60
RTGNKTELRI LKLNIEQDMG DYSCNGTNMK GSGSATVNLR VRSRLAALWP FLGIVAEVLV    120
LVTIIFIYEK RRKPDEVLDD DDGGSAPLKS NATNHKDKNV RQRNAN                  166

SEQ ID NO: 22           moltype = AA   length = 172
FEATURE                 Location/Qualifiers
source                  1..172
                        mol_type = protein
                        organism = synthetic construct
SEQUENCE: 22
IVVEGPPRIK VGKKSEHSSE GENVRLICKS ESSHPPVTEW SWFKTSDSGD QLITNSSESK     60
YVVISTADRS ELTISNLDIN SDPGTYMCNA TNTQGSVQEI MTLRVRSRLA ALWPFLGIVA    120
EVLVLVTIIF IYEKRRKPDQ TLDEDDPGAA PLKGSGHHMN DKDKNVRQRN AT           172

SEQ ID NO: 23           moltype = AA   length = 174
FEATURE                 Location/Qualifiers
source                  1..174
                        mol_type = protein
                        organism = synthetic construct
SEQUENCE: 23
INVEGPPRIK VGKKSEHASE GEFVKLICKS EASHPPVDEW VWFKTSDTGD QTISNGTEAN     60
SKYVIISTPE LSELIISDLD MNVDPGTYVC NATNSQGSAR ETISLRVRSR LAALWPFLGI    120
VAEVLVLVTI IFIYEKRRKP DQTLDEDDPG AAPLKGSGSH LNDKDKNVRQ RNAT         174

SEQ ID NO: 24           moltype = AA   length = 172
FEATURE                 Location/Qualifiers
source                  1..172
                        mol_type = protein
                        organism = synthetic construct
SEQUENCE: 24
LTVDGPPRIK AVKKSEHANE GDSVTLLCKS ESFPPFVTAWV WYKVADSGDQ VIQNGSQSRF    60
FISHSEAQSE LHIKDLDLTS DPGEYACNGT SLQGTDAAVV TLRVRSRLAA LWPFLGIVAE   120
VLVLVTVIFI YEKRRKPDEV LDDEDAGAAP LKSSGHHVND DKGKNVRQRN AS           172

SEQ ID NO: 25           moltype = AA   length = 175
FEATURE                 Location/Qualifiers
source                  1..175
                        mol_type = protein
                        organism = synthetic construct
SEQUENCE: 25
INVEGPPRIK VGKKSEHSSE GELAKLVCKS DASYPPITDW FWFKTSDTGE EEAITNSTEA     60
NGKYVVVSTP EKSQLTISNL DVNVDPGTYV CNATNAQGTT RETISLRVRS RMAALWPFLG   120
IVAEVLVLVT IIFIYEKRRK PDQTLDEDDP GAAPLKGSGT HMNDKDKNVR QRNAT        175

SEQ ID NO: 26           moltype = AA   length = 8
FEATURE                 Location/Qualifiers
source                  1..8
                        mol_type = protein
                        organism = synthetic construct
SEQUENCE: 26
DYKDDDDK                                                              8
```

The invention claimed is:

1. An anti-CD147 antibody or an antigen-binding fragment thereof, comprising:
   (1) a heavy chain CDR1 having the amino acid sequence set forth in SEQ ID NO: 7;
   (2) a heavy chain CDR2 having the amino acid sequence set forth in SEQ ID NO: 8;
   (3) a heavy chain CDR3 having the amino acid sequence set forth in SEQ ID NO: 9;
   (4) a light chain CDR1 having the amino acid sequence set forth in SEQ ID NO: 10;
   (5) a light chain CDR2 having the amino acid sequence set forth in SEQ ID NO: 11; and
   (6) a light chain CDR3 having the amino acid sequence set forth in SEQ ID NO: 12.

2. The anti-CD147 antibody or an antigen-binding fragment thereof according to claim 1, which comprises:
   (1) a heavy chain variable region having the amino acid sequence set forth in SEQ ID NO: 13; and
   (2) a light chain variable region having the amino acid sequence set forth in SEQ ID NO: 14.

3. A polynucleotide encoding the antibody or antigen-binding fragment thereof according to claim 1.

4. A pharmaceutical composition comprising the anti-CD147 antibody or antigen-binding fragment thereof according to claim 1 and a pharmaceutically acceptable carrier.

5. The pharmaceutical composition according to claim 4, wherein the pharmaceutical composition further comprises an additional therapeutic agent.

6. The pharmaceutical composition according to claim 5, wherein the additional therapeutic agent comprises an MCT inhibitor.

7. The pharmaceutical composition according to claim 4, wherein the pharmaceutical composition comprises an immune checkpoint blockade therapeutic agent.

8. A kit, comprising an anti-CD147 antibody or antigen-binding fragment according to claim 1.

9. The kit according to claim 8, wherein the kit comprises an MCT inhibitor, and/or an immune checkpoint blockade therapeutic agent.

10. A method of treating cancer in a subject in need thereof, comprising administering to the subject the anti-CD147 antibody or antigen-binding fragment thereof according to claim 1, wherein the cancer is a CD147-expressing cancer.

11. The method according to claim 10, wherein the cancer comprises cancers with expression of an immune checkpoint.

12. The method according to claim 10, wherein the cancer comprises prostate cancer, pancreatic cancer, lung cancer, breast cancer, ovarian cancer, stomach cancer, lymphoma, oesophagus cancer, bowel cancer, bone cancer.

13. The method according to claim 10, further comprising administering to the subject an MCT inhibitor before, after or at the same time as administration of an anti-CD147 antibody or antigen-binding fragment thereof, comprising a heavy chain CDR1 having the amino acid sequence set forth in SEQ ID NO 7, a heavy chain CDR2 having the amino acid sequence set forth in SEQ ID NO:8 a heavy chain CDR3 having the amino acid sequence set forth in SEQ ID NO:9, a light chain CDR1 having the amino acid sequence set forth in SEQ ID NO:410, a light chain CDR2 having the amino acid sequence set forth in SEQ ID NO:11 and a light chain CDR3 having the amino acid sequence set forth in SEQ ID NO:12.

14. The method according to claim 13, wherein the MCT inhibitor is MCT1 inhibitor, MCT3 inhibitor and/or MCT4 inhibitor.

15. The method according to claim 10, comprising administering to the subject an immune checkpoint blockade therapeutic agent before, after or at the same time as administration of an anti-CD147 antibody or antigen-binding fragment thereof, comprising a heavy chain CDR1 having the amino acid sequence set forth in SEQ ID NO:7, a heavy chain CDR2 having the amino acid sequence set forth in SEQ ID NO:8 a heavy chain CDR3 having the amino acid sequence set forth in SEQ ID NO:9, a light chain CDR1 having the amino acid sequence set forth in SEQ ID NO:10, a light chain CDR2 having the amino acid sequence set forth in SEQ ID NO:11 and a light chain CDR3 having the amino acid sequence set forth in SEQ ID NO:12.

16. The method according to claim 15, wherein the immune checkpoint blockade therapeutic agent is an anti-PD1 antibody or an anti-PDL1 antibody.

17. The method according to claim 10, wherein the subject includes humans or non-human animals.

* * * * *

UNITED STATES PATENT AND TRADEMARK OFFICE
CERTIFICATE OF CORRECTION

PATENT NO. : 12,357,691 B2
APPLICATION NO. : 18/887598
DATED : July 15, 2025
INVENTOR(S) : Xiangai Zhou Page 1 of 1

It is certified that error appears in the above-identified patent and that said Letters Patent is hereby corrected as shown below:

In the Claims

Column 30, Claim 13, Line 16:
"SEQ ID NO:8" should read: -- SEQ ID NO:8, --.

Column 30, Claim 13, Line 19:
"SEQ ID NO:410" should read: -- SEQ ID NO:10, --.

Column 30, Claim 14, Line 24:
"MCT1" should read: -- an MCT1, --.

Column 30, Claim 15, Line 33:
"SEQ ID NO:8" should read: -- SEQ ID NO:8, --.

Signed and Sealed this
Thirtieth Day of September, 2025

John A. Squires
*Director of the United States Patent and Trademark Office*